United States Patent
Jarrahi et al.

(10) Patent No.: US 11,906,424 B2
(45) Date of Patent: Feb. 20, 2024

(54) METHOD FOR IDENTIFYING CHEMICAL AND STRUCTURAL VARIATIONS THROUGH TERAHERTZ TIME-DOMAIN SPECTROSCOPY

(71) Applicant: The Regents of the University of California, Oakland, CA (US)

(72) Inventors: Mona Jarrahi, Los Angeles, CA (US); Nezih Tolga Yardimci, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/754,053

(22) PCT Filed: Oct. 1, 2020

(86) PCT No.: PCT/US2020/053860
§ 371 (c)(1),
(2) Date: Mar. 22, 2022

(87) PCT Pub. No.: WO2021/067635
PCT Pub. Date: Apr. 8, 2021

(65) Prior Publication Data
US 2023/0016600 A1    Jan. 19, 2023

Related U.S. Application Data

(60) Provisional application No. 62/909,038, filed on Oct. 1, 2019.

(51) Int. Cl.
*G01N 21/3586* (2014.01)
*G01J 3/42* (2006.01)
*G01N 21/88* (2006.01)

(52) U.S. Cl.
CPC ........... *G01N 21/3586* (2013.01); *G01J 3/42* (2013.01); *G01N 21/8851* (2013.01); *G01J 2003/423* (2013.01); *G01N 2021/8883* (2013.01)

(58) Field of Classification Search
CPC .......... G01N 21/3586; G01N 21/8851; G01N 2021/8883; G01N 33/02; G01N 21/8914;
(Continued)

(56) References Cited

U.S. PATENT DOCUMENTS 6,173,604 B1    1/2001    Xiang et al.
6,529,093 B2    3/2003    Ma
(Continued)

FOREIGN PATENT DOCUMENTS

CN    107561032 A    1/2018
EP    1804347 A1    7/2007
(Continued)

OTHER PUBLICATIONS

Yardimci et al., "Large Area Plasmonic Photoconductive Emitters for Generating High Power Broadband Terahertz Radiation", Frontiers in Optics, 2014, 2 Pgs, doi: https://doi.org/10.1364/FIO.2014.FTh3E.5.
(Continued)

*Primary Examiner* — Md M Rahman

(57) ABSTRACT

A terahertz scanner for detecting irregularities, such as chemical or structural variations, in a sample and methods of use thereof are described. The described terahertz scanner and algorithms allow for direct, high-sensitivity, high-throughput, and non-invasive detection of irregularities that range from chemical contaminant to material defects in a variety of substrates and settings.

24 Claims, 18 Drawing Sheets

(58) Field of Classification Search
CPC .......... G01N 21/94; G01N 2201/1296; G01N 22/00; G01J 3/42; G01J 2003/423; G01J 3/28
USPC ...................................................... 356/237.1
See application file for complete search history.

(56) References Cited

U.S. PATENT DOCUMENTS

| | | | |
|---|---|---|---|
| 7,321,275 | B2 | 1/2008 | Chou et al. |
| 7,515,801 | B2 | 4/2009 | McCaughan et al. |
| 7,599,409 | B2 | 10/2009 | Nishizawa et al. |
| 7,710,637 | B2 | 5/2010 | Ikari et al. |
| 7,834,722 | B2 | 11/2010 | Millet |
| 7,915,641 | B2 | 3/2011 | Otsuji et al. |
| 8,450,687 | B2 | 5/2013 | Lampin et al. |
| 8,466,528 | B2 | 6/2013 | Okamoto et al. |
| 8,514,403 | B2 | 8/2013 | Ogawa et al. |
| 8,581,784 | B2 | 11/2013 | Nagel |
| 8,610,094 | B2 | 12/2013 | Kim et al. |
| 8,649,414 | B2 | 2/2014 | Park |
| 8,730,567 | B2 | 5/2014 | Kim et al. |
| 9,804,026 | B2 | 10/2017 | Jarrahi et al. |
| 9,859,079 | B2 | 1/2018 | Jarrahi et al. |
| 10,120,263 | B2 | 11/2018 | Jarrahi |
| 10,863,895 | B2 | 12/2020 | Jarrahi |
| 11,112,305 | B2 | 9/2021 | Jarrahi et al. |
| 11,231,318 | B2 | 1/2022 | Jarrahi et al. |
| 2001/0011704 | A1 | 8/2001 | Niwa et al. |
| 2003/0184328 | A1 | 10/2003 | Lee et al. |
| 2004/0095147 | A1 | 5/2004 | Cole |
| 2005/0236260 | A1 | 10/2005 | Pasch et al. |
| 2006/0153262 | A1 | 7/2006 | Barbieri et al. |
| 2007/0216422 | A1 | 9/2007 | Sekiguchi |
| 2007/0278075 | A1 | 12/2007 | Terano et al. |
| 2008/0001691 | A1 | 1/2008 | Hong et al. |
| 2008/0277672 | A1 | 11/2008 | Hovey et al. |
| 2009/0259102 | A1 | 10/2009 | Koninckx et al. |
| 2009/0261362 | A1 | 10/2009 | Ueda et al. |
| 2009/0273532 | A1 | 11/2009 | Mendis et al. |
| 2010/0002739 | A1 | 1/2010 | Hu et al. |
| 2010/0017922 | A1 | 1/2010 | Shin et al. |
| 2010/0102256 | A1 | 4/2010 | Andrew et al. |
| 2010/0277726 | A1 | 11/2010 | Logan et al. |
| 2011/0028824 | A1 | 2/2011 | Cole et al. |
| 2011/0074293 | A1 | 3/2011 | Hagmann et al. |
| 2011/0080329 | A1 | 4/2011 | Nagel |
| 2011/0141468 | A1 | 6/2011 | Kukushkin et al. |
| 2011/0149368 | A1 | 6/2011 | Kim et al. |
| 2011/0215246 | A1 | 9/2011 | Kajiki |
| 2012/0122259 | A1 | 5/2012 | Tung et al. |
| 2012/0147907 | A1 | 6/2012 | Kim et al. |
| 2012/0162747 | A1 | 6/2012 | Kim et al. |
| 2012/0205767 | A1 | 8/2012 | Bai et al. |
| 2012/0294549 | A1 | 11/2012 | Doepke |
| 2013/0015375 | A1 | 1/2013 | Avouris et al. |
| 2013/0161514 | A1 | 6/2013 | Kukushkin et al. |
| 2013/0161541 | A1 | 6/2013 | Kim et al. |
| 2013/0284929 | A1 | 10/2013 | Ouchi |
| 2014/0103211 | A1 | 4/2014 | Darcie et al. |
| 2014/0198973 | A1 | 7/2014 | Zhang et al. |
| 2014/0346357 | A1 | 11/2014 | Jarrahi et al. |
| 2015/0316475 | A1 | 11/2015 | Rahman et al. |
| 2016/0064110 | A1 | 3/2016 | Schmadel et al. |
| 2016/0116406 | A1 | 4/2016 | Hunt et al. |
| 2016/0196943 | A1 | 7/2016 | Jarrahi et al. |
| 2016/0305869 | A1 | 10/2016 | Mann et al. |
| 2017/0123292 | A1* | 5/2017 | Jarrahi .................. G02F 1/3534 |
| 2017/0131718 | A1 | 5/2017 | Matsumura et al. |
| 2018/0058931 | A1 | 3/2018 | Jarrahi et al. |
| 2019/0150719 | A1* | 5/2019 | Jarrahi ...................... G01J 3/42 |
| 2020/0064259 | A1 | 2/2020 | Jarrahi et al. |
| 2020/0264048 | A1 | 8/2020 | Jarrahi et al. |
| 2023/0003642 | A1 | 1/2023 | Jarrahi et al. |

FOREIGN PATENT DOCUMENTS

| | | |
|---|---|---|
| EP | 2807675 A1 | 12/2014 |
| EP | 3155702 A1 | 4/2017 |
| EP | 3302224 A2 | 4/2018 |
| EP | 3312590 A1 | 4/2018 |
| EP | 2807675 B1 | 9/2018 |
| EP | 3612812 A1 | 2/2020 |
| EP | 3302224 B1 | 10/2020 |
| EP | 3155702 B1 | 12/2020 |
| EP | 4038366 A1 | 8/2022 |
| EP | 4052458 A1 | 9/2022 |
| JP | 11056786 A | 3/1999 |
| JP | 2002511690 A | 4/2002 |
| JP | 2002511960 A | 4/2002 |
| JP | 2006216646 A | 8/2006 |
| JP | 2008122278 A | 5/2008 |
| JP | 2009105102 A | 5/2009 |
| JP | 2009531841 A | 9/2009 |
| JP | 2010510703 A | 4/2010 |
| JP | 2014112078 A | 6/2014 |
| JP | 2015513067 A | 4/2015 |
| JP | 6169614 B2 | 7/2017 |
| JP | 2017523601 A | 8/2017 |
| JP | 2018516667 A | 6/2018 |
| JP | 6860210 B2 | 3/2021 |
| JP | 6955337 B2 | 10/2021 |
| KR | 1020080004467 A | 1/2008 |
| WO | 9846042 A1 | 10/1998 |
| WO | 2005019810 A2 | 3/2005 |
| WO | 2005019810 A3 | 5/2005 |
| WO | 2006030608 A1 | 3/2006 |
| WO | 2010011186 A1 | 1/2010 |
| WO | 2010021073 A1 | 2/2010 |
| WO | 2010044193 A1 | 4/2010 |
| WO | 2011028179 A1 | 3/2011 |
| WO | 2011118398 A1 | 9/2011 |
| WO | 2011129690 A2 | 10/2011 |
| WO | 2012057710 A1 | 5/2012 |
| WO | 2013112608 A1 | 8/2013 |
| WO | 2013116924 A1 | 8/2013 |
| WO | 2015021100 A1 | 2/2015 |
| WO | 2015192094 | 12/2015 |
| WO | 2016196309 A2 | 12/2016 |
| WO | 2016196309 A3 | 2/2017 |
| WO | 2018195429 A1 | 10/2018 |
| WO | 2019008570 A1 | 1/2019 |
| WO | 2021067635 A1 | 4/2021 |
| WO | 2021087459 A1 | 5/2021 |

OTHER PUBLICATIONS

Yardimci et al., "Nanostructure-Enhanced Photoconductive Terahertz Emission and Detection", Small, vol. 14, Aug. 29, 2018, pp. 1802437-1-1802437-14, doi: https://doi.org/10.1002/smll.201802437.

Yardimci et al., "Plasmonics Enhanced Terahertz Radiation from Large Area Photoconductive Emitters", IEEE, 2014, pp. 326-327, doi: 10.1109/IPCon.2014.6995376.

Yu et al., "The Potential of Terahertz Imaging for Cancer Diagnosis: A Review of Investigations to Date", Quantitative Imaging in Medicine and Surgery, vol. 2, No. 1, Mar. 2012, pp. 33-45, doi: 10.3978/j.issn.2223-4292.2012.01.04.

Zhang et al., "Simultaneous Determination of Amino Acid Mixtures in Cereal by Using Terahertz Time Domain Spectroscopy and Chemometrics", Chemometrics and Intelligent Laboratory Systems, vol. 164, Mar. 7, 2017, pp. 8-15, doi: https://dx.doi.org/10.1016/j.chemolab.2017.03.001.

European Examination Report Corresponding to EP Application No. 13741491.8, dated Oct. 21, 2015, 5 Pages.

Extended European Search Report for European Application No. 15807544.0, Search completed Jun. 12, 2018, and dated Jun. 20, 2018, 8 Pgs.

Extended European Search Report for European Application No. 16804130.9, Search completed Jan. 16, 2019, dated Jan. 25, 2019, 6 Pgs.

(56) References Cited

OTHER PUBLICATIONS

Extended European Search Report for European Application No. 18787213.0, Search completed Nov. 30, 2020, dated Dec. 9, 2020, 7 Pgs.
Unknown Author, "Xilinx and Altera FPGA Integration Modules", Opal Kelly, Apr. 2023, Retrieved from the Internet <https://www.opalkelly.com/>, 7 Pgs.
International Preliminary Report on Patentability for International Application PCT/US2020/053860, dated Apr. 5, 2022, dated Apr. 14, 2022, 8 Pgs.
International Preliminary Report on Patentability for International Application PCT/US2020/058549, dated May 3, 2022, dated May 12, 2022, 12 Pgs.
International Preliminary Report on Patentability for International Application PCT/US2013/022776, dated Jul. 29, 2014, dated Aug. 7, 2014, 8 Pgs.
International Preliminary Report on Patentability for International Application PCT/US2014/049866, dated Feb. 9, 2016, dated Feb. 18, 2016, 8 Pgs.
International Preliminary Report on Patentability for International Application PCT/US2015/035685, dated Dec. 15, 2016, dated Dec. 22, 2016, 7 Pgs.
International Preliminary Report on Patentability for International Application PCT/US2016/034704, dated Nov. 28, 2017, dated Dec. 7, 2017, 10 Pgs.
International Preliminary Report on Patentability for International Application PCT/US2018/028579, dated Oct. 22, 2019, dated Oct. 31, 2019, 8 Pgs.
International Search Report and Written Opinion for International Application PCT/US2015/035685, dated Aug. 27, 2015, dated Aug. 27, 2015, 8 Pgs.
International Search Report and Written Opinion for International Application No. PCT/US2020/053860, dated Nov. 30, 2020, dated Jan. 6, 2021, 14 Pgs.
International Search Report and Written Opinion for International Application No. PCT/US2020/058549, dated Feb. 16, 2021, date Mar. 23, 2021, 18 Pgs.
International Search Report and Written Opinion for International Application No. PCT/US2013/022776, dated May 15, 2013, dated May 16, 2013, 9 Pgs.
International Search Report and Written Opinion for International Application No. PCT/US2014/049866, dated Nov. 19, 2014, dated Nov. 20, 2014, 9 Pgs.
International Search Report and Written Opinion for International Application No. PCT/US2016/034704, dated Dec. 26, 2016, dated Dec. 26, 2016, 11 Pgs.
International Search Report and Written Opinion for International Application No. PCT/US2018/028579, dated Jul. 5, 2018, dated Jul. 20, 2018, 11 Pgs.
Supplementary European Search Report for European Application No. 13741491.8, dated Sep. 28, 2015, dated Oct. 12, 2015, 6 Pgs.
Unknown Author, "Mycotoxins: Risks in Plant, Animal, and Human Systems", Council for Agricultural Science and Technology, Task Force Report, No. 139, Jan. 2003, 217 Pgs (presented in 2 parts).
Ajito et al., "THz Chemical Imaging for Biological Applications", IEEE Transactions on Terahertz Science and Technology, vol. 1, No. 1, Sep. 2011, pp. 293-300, doi: 10.1109/TTHZ.2011.2159562.
Alshannaq et al., "Controlling Aflatoxin Contamination and Propagation of Aspergillus Flavus by a Soy-Fermenting Aspergillus Oryzae Strain", Scientific Reports, vol. 8, No. 16871, Nov. 15, 2018, pp. 1-14, doi: 10.1038/s41598-018-35246-1.
Anastasi et al., "Terahertz NDE for Metallic Surface Roughness Evaluation", SPIE 11th Annual International Symposium on Nondestructive Evaluation for Health Monitoring and Diagnostics, Jun. 19, 2006, pp. 57-62.
Anastasi et al., "Terahertz NDE for Under Paint Corrosion Detection and Evaluation", Annual Review of Progress in Quantitative Nondestructive Evaluation, Jul. 21 - Aug. 4, 2005, pp. 49-56.
Arbab et al., "Terahertz Spectroscopy for the Assessment of Burn Injuries in Vivo", Journal of Biomedical Optics, vol. 18, No. 7, Jul. 2013, p. 077004-1-077004-7, doi: 10.1117/1.JBO.18.7.077004.
Ashworth et al., "Terahertz Pulsed Spectroscopy of Freshly Excised Human Breast Cancer", Optics Express, vol. 17, No. 15, Jul. 20, 2009, p. 12444-12454, doi: https://doi.org/10.1364/OE.17.012444.
Asner et al., "Progressive Forest Canopy Water Loss during the 2012-2015 California Drought", Proceedings of the National Academy of Sciences, Dec. 28, 2015, pp. E249-E255, doi: www.pnas.org/cgi/doi/10.1073/pnas.1523397113.
Baek et al., "Detection of Melamine in Foods Using Terahertz Time-Domain Spectroscopy", Journal of Agriculture and Food Chemistry, vol. 62, Jun. 2, 2014, pp. 5403-5407, doi: dx.doi.org/10.1021/jf501170z.
Baker et al., "Self-Triggered Asynchronous Optical Sampling Terahertz Spectroscopy Using a Bidirectional Mode-locked Fiber Laser", Scientific Reports, vol. 8, No. 14802, Oct. 4, 2018, pp. 1-8, doi: 10.1038/s41598-018-33152-0.
Baldacci et al., "Non-Invasive Absolute Measurement of Leaf Water Content Using Terahertz Quantum Cascade Lasers", Plant Methods, vol. 13, No. 51, Jun. 17, 2017, pp. 1-7, doi: 10.1186/s13007-017-0197-z.
Bartlett et al., "The Correlations and Sequence of Plant Stomatal, Hydraulic, and Wilting Responses to Drought", The Proceedings of the National Academy of Sciences, vol. 113, No. 46, Nov. 15, 2016, p. 13098-13103, doi: www.pnas.org/cgi/doi/10.1073/pnas.1604088113.
Bartlett et al., "The Determinants of Leaf Turgor Loss Point and Prediction of Drought Tolerance of Species and Biomes: A Global Meta-Analysis", Ecology Letters, vol. 15, 2012, pp. 393-405, doi: 10.1111/j.1461-0248.2012.01751.x.
Beck et al., "Impulsive Terahertz Radiation with High Electric Fields from an Amplifier-Driven Large-Area Photoconductive Antenna", Optics Express, vol. 18, No. 9, Apr. 26, 2010, pp. 9251-9257, doi: https://doi.org/10.1364/OE.18.009251.
Bennett et al., "Aflatoxins: Background, Toxicology, and Molecular Biology", Foodborne Diseases, Humana Press Inc., 2007, pp. 355-373, doi: 10.1007/978-1-59745-501-5_13.
Berry et al., "Design, Fabrication, and Experimental Characterization of Plasmonic Photoconductive Terahertz Emitters", Journal of Visualized Experiments, vol. 77, No. e50517, Jul. 2013, pp. 1-8, doi: 10.3791/50517.
Berry et al., "Generation of High Power Pulsed Terahertz Radiation Using a Plasmonic Photoconductive Emitter Array with Logarithmic Spiral Antennas", Applied Physics Letters, vol. 104, 2014, p. 081122-1 - 081122-4, doi: http://dx.doi.org/10.1063/1.4866807.
Berry et al., "High Power Terahertz Generation Using 1550 nm Plasmonic Photomixers", Applied Physics Letters, vol. 105, Jul. 10, 2014, p. 011121-1-011121-4, doi: http://dx.doi.org/10.1063/1.4890102.
Berry et al., "Nanoscale Contact Electrodes for Significant Radiation Power Enhancement in Photoconductive Terahertz Emitters", IEEE, 2013, 4 Pgs.
Berry et al., "Plasmonic Photomixers for Increased Terahertz Radiation Powers At 1550 nm Optical Pump Wavelength", IEEE, 2014, 2 Pgs.
Berry et al., "Plasmonically-Enhanced Localization of Light into Photoconductive Antennas", IEEE, 2010, 2 Pgs.
Berry et al., "Plasmonics Enhanced Photomixing for Generating Quasi-Continuous-Wave Frequency-Tunable Terahertz Radiation", Optics Letters, vol. 39, No. 15, Aug. 1, 2014, pp. 4522-4524, doi: http://doi.org/10.1364/OL.39.004522.
Berry et al., "Principles of Impedance Matching in Photoconductive Antennas", Journal of Infrared, Millimeter, and Terahertz Waves, vol. 33, Sep. 27, 2012, pp. 1182-1189, doi: 10.1007/s10762-012-9937-3.
Berry et al., "Significant Performance Enhancement in Photoconductive Terahertz Optoelectronics by Incorporating Plasmonic Contact Electrodes", Nature Communication, vol. 4, No. 1622, Mar. 27, 2013, pp. 1-10, doi: 10.1038/ncomms2638.
Berry et al., "Terahertz Generation Using Plasmonic Photoconductive Gratings", New Journal of Physics, vol. 14, No. 105029, Oct. 30, 2012, pp. 1-12, doi: 10.1088/1367-2630/14/10/105029.

(56) References Cited

OTHER PUBLICATIONS

Berry et al., "Ultrafast Photoconductors based on Plasmonic Gratings", IEEE, 2011, 2 Pgs.

Bioucas-Dias et al., "Two-Step Algorithms for Linear Inverse Problems with Non-Quadratic Regularization", IEEE, 2007, 4 Pgs.

Bjarnason et al., "ErAs: GaAs Photomixer with Two-Decade Tunability and 12 uW Peak Output Power", Applied Physics Letters, vol. 85, No. 18, Nov. 1, 2004, pp. 3983-3985, doi: 10.1063/1.1813635.

Born et al., "Monitoring Plant Drought Stress Response Using Terahertz Time-Domain Spectroscopy", Plant Physiology, vol. 164, Apr. 2014, pp. 1571-1577, doi: https://doi.org/10.1104/pp. 113.233601.

Brown et al., "Characterization of a Planar Self-Complementary Square- Spiral Antenna in the THz Region", Microwave and Optical Technology Letters, vol. 48, No. 3, Mar. 2006, pp. 524-529, doi: 10.1002/mop.

Brown et al., "Coherent Millimeter-Wave Generation by Heterodyne Conversion in Low-Temperature-Grown GaAs Photoconductors", Journal of Applied Physics, vol. 73, No. 3, Feb. 1, 1993, pp. 1480-1484.

Cassel et al., "Aflatoxins: Hazards in Grain/Aflatoxicosis and Livestock", South Dakota State University, Fact Sheets, Paper 86, Oct. 1, 2001, 5 Pgs.

Castro-Camus et al., "Leaf Water Dynamics of Arabidopsis Thaliana Monitored in-Vivo Using Terahertz Time-Domain Spectroscopy", Scientific Reports, vol. 3, No. 2910, Oct. 9, 2013, pp. 1-5, doi: 10.1038/srep02910.

Catrysse et al., "Guided Modes Supported by Plasmonic Films with a Periodic Arrangement of Subwavelength Slits", Applied Physics Letters, vol. 88, 2006, p. 031101-1 - 031101-3, doi: 10.1063/1.2164905.

Chan et al., "Imaging with Terahertz Radiation", Reports on Progress in Physics, vol. 70, Jul. 12, 2007, pp. 1325-1379, doi: 10.1088/0034-4885/70/8/R02.

Chen et al., "A preliminary Study of Aflatoxin B1 Detection in Peanut Oil by Terahertz Time-Domain Spectroscopy", Transactions of the ASABE, vol. 57, No. 6, 2014, pp. 1793-1799, doi: 10.13031/trans.57.10725.

Chen et al., "Total Variation Deconvolution for Terahertz Pulsed Imaging", Inverse Problems in Science and Engineering, vol. 19, No. 2, Mar. 2011, pp. 223-232, doi: 10.1080/17415977.2010.550045.

Chimot et al., "Photomixing at 1.55 um in Ion-Irradiated In0.53GA0.47As on InP", Optics Express, vol. 14, No. 5, Mar. 6, 2006, pp. 1856-1861.

Claudio et al., "Monitoring Drought Effects on Vegetation Water Content and Fluxes in Chaparral with the 970 nm Water Band Index", Remote Sensing of Environment, vol. 103, Aug. 15, 2006, pp. 304-311, doi: 10.1016/j.rse.2005.07.015.

Clothier et al., "Effects of THz Exposure on Human Primary Keratinocyte Differentiation and Viability", Journal of Biological Physics, vol. 29, 2003, pp. 179-185.

Cotrozzi et al., "Using Foliar Spectral Properties to Assess the Effects of Drought on Plant Water Potential", Tree Physiology, vol. 37, Sep. 19, 2017, pp. 1582-1591, doi: https://doi.org/10.1093/treephys/tpx106.

Danson et al., "High-Spectral Resolution Data for Determining Leaf Water Content", International Journal of Remote Sensing, vol. 13, No. 3, 1992, pp. 461-470, doi: https://doi.org/10.1080/01431169208904049.

Delmulle et al., "Development of an Immunoassay-Based Lateral Flow Dipstick for the Rapid Detection of Aflatoxin B1 in Pig Feed", Journal of Agricultural and Food Chemistry, vol. 53, Apr. 8, 2005, pp. 3364-3368, doi: https://doi.org/10.1021/jf0404804.

Dreyhaupt et al., "High-Intensity Terahertz Radiation from a Microstructured Large-Area Photoconductor", Applied Physics Letters, vol. 86, 2005, pp. 121114-1-121114-3, doi: 10.1063/1.1891304.

Fitzgerald et al., "Catalogue of Human Tissue Optical Properties at Terahertz Frequencies", Journal of Biological Physics, vol. 29, 2003, pp. 123-128, doi: 10.1023/A:1024428406218.

Fitzgerald et al., "Nondestructive Analysis of Tablet Coating Thicknesses Using Terahertz Pulsed Imaging", Journal of Pharmaceutical Sciences, vol. 94, No. 1, Jan. 2005, pp. 177-183, doi: 10.1002/jps.20225.

Unknown Author, "Guidance for Industry: Action levels for Poisonous or Deleterious Substances in Human food and Animal Feed", Food and Drug Administration, Aug. 2000, 18 Pgs.

Ge et al., "Quantitative Determination of Aflatoxin B1 Concentration in Acetonitrile by Chemometric Methods Using Terahertz Spectroscopy", Food Chemistry, vol. 209, 2016, pp. 286-292, doi: https://doi.org/10.1016/j.foodchem.2016.04.070.

Gente et al., "Contactless Water Status Measurements on Plants at 35 GHz", Journal of Infrared, Millimeter, and Terahertz Waves, vol. 36, 2015, pp. 312-317, doi: 10.1007/s10762-014-0127-3.

Gente et al., "Determination of Leaf Water Content from Terahertz Time- Domain Spectroscopic Data", Journal of Infrared, Millimeter, and Terahertz Waves, 2013, pp. 1-8.

Gente et al., "Outdoor Measurements of Leaf Water Content Using THz Quasi Time-Domain Spectroscopy", Journal of Infrared, Millimeter, and Terahertz Waves, vol. 39, Jul. 17, 2018, pp. 943-948, doi: https://doi.org/10.1007/s10762-018-0520-4.

Gowen et al., "Terahertz Time Domain Spectroscopy and Imaging: Emerging Techniques for Food Process Monitoring and Quality Control", Trends in Food Science & Technology, vol. 25, 2012, pp. 40-46, doi: 10.1016/j.tifs.2011.12.006.

Gregory et al., "Optimization of Photomixers and Antennas for Continuous-Wave Terahertz Emission", IEEE Journal of Quantum Electronics, vol. 41, No. 5, May 2005, pp. 717-728, doi: 10.1109/JQE.2005.844471.

Grischkowsky et al., "Far-Infrared Time-Domain Spectroscopy with Terahertz Beams of Dielectrics and Semiconductors", Journal of the Optical Society of America B, vol. 7, No. 10, Oct. 1990, pp. 2006-2015, doi: https://doi.org/10.1364/JOSAB.7.002006.

Gu et al., "Detection of Terahertz Radiation from Longitudinal Optical Phonon- Plasmon Coupling Modes in InSb Film Using an Ultrabroadband Photoconductive Antenna", Applied Physics Letters, vol. 77, No. 12, Sep. 18, 2000, pp. 1798-1800.

Hadjiloucas et al., "Measurements of Leaf Water Content Using Terahertz Radiation", IEEE Transactions on Microwave Theory and Techniques, vol. 47, No. 2, Feb. 1999, pp. 142-149, doi: 10.1109/22.744288.

Heshmat et al., "Nanoplasmonic Terahertz Photoconductive Switch on GaAs", Nano Letters, vol. 12, Nov. 21, 2012, pp. 6255-6259, doi: dx.doi.org/10.1021/nl303314a.

Howell, David "EV Everywhere Grand Challenge—Battery Status and Cost Reduction Prospects", U.S. Department of Energy, Jul. 26, 2012, Retrieved from the Internet <https://www1.eere.energy.gov/vehiclesandfuels/pdfs/ev_everywhere/5_howell b.pdf>, 15 Pgs.

Hsieh et al., "Analysis of Periodic metallic nano-slits for efficient interaction of terahertz and optical waves at nano-scale dimensions", Journal of Applied Physics, vol. 109, 2011, pp. 084326-1-084326-5.

Hsieh et al., "Electrochemical-Acoustic Time of Flight: in Operando Correlation of Physical Dynamics with Battery Charge and Health", Energy & Environmental Science, vol. 8, 2015, pp. 1569-1577, doi: 10.1039/c5ee00111k.

Hu et al., "Imaging with Terahertz Waves", Optics Letters, vol. 20, No. 16, Aug. 15, 1995, pp. 1716-1718, doi: https://doi.org/10.1364/OL.20.001716.

Huang et al., "Tissue Characterization Using Terahertz Pulsed Imaging in Reflection Geometry", Physics in Medicine and Biology, vol. 54, 2009, pp. 149-160, doi: 10.1088/0031-9155/54/1/010.

Humphreys et al., "Medical Applications of Terahertz Imaging: A Review of Current Technology and Potential Applications in Biomedical Engineering", Proceedings of the 26th Annual International Conference of the IEEE EMBS San Francisco, CA, USA Sep. 1-5, 2004, pp. 1302-1305.

(56) References Cited

OTHER PUBLICATIONS

Hunt, Jr. et al., "Detection of Changes in Leaf Water Content Using Near- and Middle-Infrared Reflectances", Remote Sensing of Environment, vol. 30, 1989, pp. 43-54, doi: https://doi.org/10.1016/0034-4257(89)90046-1.

Hunt, Jr. et al., "Measurement of Leaf Relative Water Content by Infrared Reflectance", Remote Sensing of Environment, vol. 22, pp. 1987, 429-435.

Huo et al., "Planar Log-Periodic Antennas on Extended Hemispherical Silicon Lenses for Millimeter/Submillimeter Wave Detection Applications", International Journal of Infrared and Millimeter Waves, vol. 23, No. 6, Jun. 2002, pp. 819-839.

Jacques, Steven L. "Optical Properties of Biological Tissues: A Review", Physics in Medicine and Biology, vol. 58, May 10, 2013, pp. R37-R61, doi: 10.1088/0031-9155/58/11/R37.

Jarrahi, Mona "Advanced Photoconductive Terahertz Optoelectronics Based on Nano-Antennas and Nano-Plasmonic Light Concentrators", IEEE Transactions on Terahertz Science and Technology, vol. 5, No. 3, May 2015, pp. 391-397, doi: 10.1109/TTHZ.2015.2406117.

Jepsen et al., "Terahertz Spectroscopy and Imaging—Modern Techniques and Applications", Laser & Photonics Reviews, vol. 5, No. 1, 2011, pp. 124-166, doi: 10.1002/lpor.201000011.

Jördens et al., "Evaluation of Leaf Water Status by Means of Permittivity at Terahertz Frequencies", Journal of Biological Physics, vol. 35, Jun. 11, 2009, pp. 255-264, doi: 10.1007/s10867-009-9161-0.

Just et al., "A Method to Quantify Coating Thickness and Porosity of Electrodes for Lithium-Ion-Batteries", Measurement, vol. 89, 2016, pp. 312-315.

Kindt et al., "Far-Infrared Dielectric Properties of Polar Liquids Probed by Femtosecond Terahertz Pulse Spectroscopy", Journal of Physical Chemistry, vol. 100, 1996, p. 10373-10379.

Knipling, Edward B. "Physical and Physiological Basis for the Reflectance of Visible and Near-Infrared Radiation from Vegetation", Remote Sensing of Environment, vol. 1, 1970, pp. 155-159, doi: https://doi.org/10.1016/S0034-4257(70)80021-9.

Kokkonen et al., "Determination of Selected Mycotoxins in Mould Cheeses with Liquid Chromatography Coupled to Tandem with Mass Spectrometry", Food Additives and Contaminants, vol. 22, No. 5, May 2005, pp. 449-456, doi: 10.1080/02652030500089861.

Federici et al., "THz imaging and sensing for security applications-explosives, weapons and drugs", Semiconductor Science and Technology, Jul. 1, 2005, vol. 20, No. 7, pp. S266-S280, XP020086549, ISSN: 0268-1242, DOI: 10.1088/02681242/20/7/018.

Ren et al., "State-of-the-art in terahertz sensing for food and water security—A comprehensive review", Trends in Food Science & Technology, Jun. 8, 2005 (Jun. 8, 2005), vol. 85, pp. 241-251, XP085605185, ISSN: 0924-2244, DOI: 10.1016/J.TIFS.2019.01.019.

Zhong-Yuan et al., "Aflatoxin B1 detected by Terahertz time-domain spectroscopy", 8th International Congress on Image 7,8 and Signal Processing (LISP), IEEE, Oct. 2, 1401, pp. 1225-1230, XP032867276, DOI: 10.1109/CISP.2015.7408068.

Krimi et al., "Highly Accurate Thickness Measurement of Multi-Layered Automotive Paints Using Terahertz Technology", Applied Physics Letters, vol. 109, Jul. 12, 2016, p. 021105-1-021105-4.

Krishnamachari et al., "Hepatitis Due to Aflatoxicosis, An Outbreak in Western India", The Lancet, May 10, 1975, pp. 1061-1063, doi: 10.1016/S0140-6736(75)91829-2.

Kubiske et al., "Pressure-Volume Relationships in Non-Rehydrated Tissue at Various Water Deficits", Plant, Cell & Environment, vol. 13, May 17, 1990, pp. 995-1000.

Lecun et al., "Convolutional Networks for Images, Speech, and Time-Series", The Handbook of Brain Theory and Neural Networks, 1998, 14 Pgs.

Li et al., "A Polarization-Insensitive Plasmonic Photoconductive Terahertz Emitter", AIP Advances, vol. 7, Nov. 16, 2017, p. 115113-1-15513-6, doi: https://doi.org/10.1063/1.5006273.

Li et al., "Measurements and Analysis of Water Content in Winter Wheat Leaf Based on Terahertz Spectroscopy", International Journal of Agricultural and Biological Engineering, vol. 11, No. 3, May 2018, pp. 178-182, doi: 10.25165/j.ijabe.20181103.3520.

Liu et al., "Coherent Detection of Multiband Terahertz Radiation Using a Surface Plasmon-Polariton Based Photoconductive Antenna", IEEE Transactions on Terahertz Science and Technology, vol. 1, No. 2, Nov. 2011, pp. 412-415, doi: 10.1109/TTHZ/2011.2165241.

Loata et al., "Radiation Field Screening in Photoconductive Antennae Studied via Pulsed Terahertz Emission Spectroscopy", Applied Physics Letters, vol. 91, 2007, p. 232506-1-232506-3, doi: 10.1063/1.2823590.

Malone et al., "Determination of Aflatoxins in Grains and Raw Peanuts by a Rapid Procedure with Fluorometric Analysis", Journal of AOAC International, vol. 83, No. 1, 2000, pp. 95-98.

Mangeney et al., "Continuous Wave Terahertz Generation up to 2 THz by Photomixing on Ion-Irradiated in0.53GA0.47As at 1.55 um Wavelengths", Applied Physics Letters, vol. 91, Dec. 10, 2007, p. 241102-1-241102-3, doi: 10.1063/1.2817607.

Michael et al., "Large-Area Traveling-Wave Photonic Mixers for Increased Continuous Terahertz Power", Applied Physics Letters, vol. 86, Mar. 11, 2005, p. 111120-1-111120-3, doi: 10.1063/1.1884262.

Middendorf et al., "THz Generation Using Extrinsic Photoconductivity at 1550 nm", Optics Express, vol. 20, No. 15, Jul. 16, 2012, p. 16504-16509.

Mittleman et al., "Gas Sensing Using Terahertz Time-Domain Spectroscopy", Applied Physics B Lasers and Optics, vol. 67, Feb. 25, 1998, pp. 379-390.

Mittleman et al., "T-Ray Imaging", IEEE Journal of Selected Topics in Quantum Electronics, vol. 2, No. 3, Sep. 1996, pp. 679-689, doi: 10.1109/2944.571768.

Mohanty et al., "Non-Destructive Evaluation of Slot-Die-Coated Lithium Secondary Battery Electrodes by in-line Laser Caliper and IR Thermography Methods", Analytical Methods, vol. 6, 2014, pp. 674-683, doi: 10.1039/C3AY41140K.

Momen et al., "Interacting Effects of Leaf Water Potential and Biomass on Vegetation Optical Depth", Journal of Geophysical Research: Biogeosciences, vol. 122, Nov. 23, 2017, pp. 3031-3046, doi: https://doi.org/10.1002/2017JG004145.

Nagatsuma et al., "Terahertz Imaging Based on Optical Coherence Tomography", Photonics Research, vol. 2, No. 4, Aug. 2014, pp. B64-B69, doi: https://doi.org/10.1364/PRJ.2.000B64.

Ng, Andrew "Sparse Autoencoder", CS294A Lecture notes, 2011, 1-19.

Okyay et al., "High-Efficiency Metal-Semiconductor-Metal Photodetectors on Heteroepitaxially Grown Ge on Si", Optics Letters, vol. 31, No. 17, Sep. 1, 2006, pp. 2565-2567, doi: 10.1364/OL.31.002565.

Ollinger, S. V. "Tansley review: Sources of Variability in Canopy Reflectance and the Convergent Properties of Plants", New Phytologist, vol. 189, 2011, pp. 375-394, doi: 10.1111/j.1469-8137.2010.03536.x.

Park et al., "Enhancement of Terahertz Pulse Emission by Optical Nanoantenna", ACS Nano, vol. 6, No. 3, Feb. 17, 2012, pp. 2026-2031, doi: 10.1021/nn204542x.

Park et al., "Terahertz Photoconductive Antenna with Metal Nanoislands", Optics Express, vol. 20, No. 23, Nov. 5, 2012, p. 25530-25535.

Parrott et al., "Terahertz Spectroscopy: Its Future Role in Medical Diagnoses", Journal of Molecular Structure, vol. 1006, Jun. 13, 2011, pp. 66-76, doi: 10.1016/j.molstruc.2011.05.048.

Pearson et al., "Detecting Aflatoxin in Single Corn Kernels by Transmittance and Reflectance Spectroscopy", Transactions of the ASAE, vol. 44, No. 5, 2001, pp. 1247-1254, doi: 10.13031/2013.6418.

Peñuelas et al., "Reflectance Indices Indicative of Changes in Water and Pigment Contents of Peanut and Wheat Leaves", Photosynthetica, vol. 36, No. 3, 1999, pp. 355-360, doi: 10.1023/A:1007033503276.

Peñuelas et al., "The Reflectance at the 950-970 nm Region as an Indicator of Plant Water Status", International Journal of Remote Sensing, vol. 14, No. 10, 1993, pp. 1887-1905.

(56) References Cited

OTHER PUBLICATIONS

Peter et al., "Coherent Terahertz Detection with a Large-Area Photoconductive Antenna", Applied Physics Letters, vol. 91, No. 081109, Aug. 21, 2007, pp. 40-42, doi: 10.1063/1.2772783.
Peytavit et al., "Continuous Terahertz-Wave Generation Using a Monolithically Integrated Horn Antenna", Applied Physics Letters, vol. 93, Sep. 16, 2008, p. 111108-1-111108-3, doi: 10.1063/1.2983741.
Peytavit et al., "Milliwatt-Level Output Power in the Sub-Terahertz Range Generated by Photomixing in a GaAs Photoconductor", Applied Physics Letters, vol. 99, 2011, p. 223508-1-223508-3, doi: 10.1063/1.3664635.
Pickwell-MacPherson, Emma "Practical Considerations for in Vivo THz Imaging", Terahertz Science and Technology, vol. 3, No. 4, Dec. 2010, pp. 163-171, doi: 10.11906/TST.163-171.2010.12.16.
Pietsch et al., "X-Ray Tomography for Lithium Ion Battery Research: A Practical Guide", Annual Review of Materials Research, vol. 47, 2017, pp. 451-479.
Preu et al., "1550 nm ErAs:In(Al)GaAs Large Area Photoconductive Emitters", Applied Physics Letters, vol. 101, 2012, p. 101105-1-101105-4, doi: https://doi.org/10.1063/1.4750244.
Preu et al., "Tunable, Continuous-Wave Terahertz Photomixer Sources and Applications", Journal of Applied Physics, vol. 109, Mar. 22, 2011, p. 016301-1-061301-56, doi: 10.1063/1.3552291.
Pupeza et al., "Highly Accurate Optical Material Parameter Determination with THz Time-Domain Spectroscopy", Optics Express, vol. 15, No. 7, Apr. 2, 2007, pp. 4335-4350, doi: 10.1364/oe.15.004335.
Qu et al., "Function of Terahertz Spectra in Monitoring the Decomposing Process of Biological Macromolecules and in Investigating the Causes of Photoinhibition", Science China Life Sciences, vol. 60, No. 3, Mar. 2017, pp. 307-312, doi: 10.1007/s11427-016-0057-9.
Qu et al., "Review of Theoretical Methods and Research Aspects for Detecting Leaf Water Content Using Terahertz Spectroscopy and Imaging", International Journal of Agricultural and Biological Engineering, vol. 11, No. 5, Sep. 2018, pp. 27-34, doi: 10.25165/j.ijabe.20181105.3952.
Rao et al., "Satellite-Based Vegetation Optical Depth as an Indicator of Drought-Driven Tree Mortality", Remote Sensing of Environment, vol. 227, Apr. 13, 2019, pp. 125-136, doi: https://doi.org/10.1016/j.rse.2019.03.026.
Rapaport et al., "Combining Leaf Physiology, Hyperspectral Imaging and Partial Least Squares-Regression (PLS-R) for Grapevine Water Status Assessment", ISPRS Journal of Photogrammetry and Remote Sensing, vol. 109, Sep. 27, 2015, pp. 88-97, doi: https://doi.org/10.1016/j.isprsjprs.2015.09.003.
Rapaport et al., "The Potential of the Spectral 'Water Balance Index' (WABI) for Crop Irrigation Scheduling", New Phytologist, 2017, pp. 1-16, doi: 10.1111/nph.14718.
Roehle et al., "Next Generation 1.5 um Terahertz Antennas: Mesa-Structuring of InGaAs/InAlAs Photoconductive Layers", Optics Express, vol. 18, No. 3, Feb. 1, 2010, pp. 2296-2301.
Ronne et al., "THz Spectroscopy of Liquid H20 and D20", Physical Review Letters, vol. 82, No. 14, Apr. 5, 1999, pp. 2888-2891, doi: 10.1103/PhysRevLett.82.2888.
Sack et al., "ABA Accumulation in Dehydrating Leaves is Associated with Decline in Cell Volume, Not Turgor Pressure", Plant Physiology, vol. 176, Jan. 2018, pp. 489-495, doi: www.plantphysiol.org/cgi/doi/10.1104/pp. 17.01097.
Sack et al., "Leaf Pressure-Volume Curve Parameters", Prometheus Wiki, 2017, pp. 1-2.
Sancho-Knapik et al., "Microwave L-Band (1730 MHz) Accurately Estimates the Relative Water Content in Poplar Leaves. A Comparison with a Near Infrared Water Index (R1300/R1450)", Agricultural and Forest Meteorology, vol. 151, Jul. 27, 2011, pp. 827-832, doi: 10.1016/j.agrformet.2011.01.016.
Santesteban et al., "Terahertz time Domain Spectroscopy Allows Contactless Monitoring of Grapevine Water Status", Frontiers in Plant Science, vol. 6, No. 404, Jun. 2015, pp. 1-9, doi: 10.3389/fpls.2015.00404.
Schindelin et al., "Fiji—An Open-Source Platform for Biological-Image Analysis", Nature Methods, vol. 9, No. 7, Dec. 7, 2013, pp. 1-15, doi: 10.1038/nmeth.2019.
Schmale, III et al., "Mycotoxins in Crops: A Threat to Human and Domestic Animal Health", The Plant Health Instructor, 2009, 19 Pgs, doi: 10.1094/PHI-I-2009-0715-01.
Scoffoni et al., "Dynamics of Leaf Hydraulic Conductance with Water Status: Quantification and Analysis of Species Differences Under Steady State", Journal of Experimental Botany, vol. 63, No. 2, 2012, pp. 643-658, doi: 10.1093/jxb/err270.
Scoffoni et al., "Leaf Shrinkage with Dehydration: Coordination with Hydraulic Vulnerability and Drought Tolerance", Plant Physiology, vol. 164, Apr. 2014, pp. 1772-1788, doi: ww.plantphysiol.org/doi/10.1104/pp. 113.221424.
Shen et al., "Properties of a One-Dimensional Metallophotonic Crystal", Physical Review B, vol. 70, 2004, p. 035101-1-038101-8, doi: 10.1103/PhysRevB.70.035101.
Shibuya et al., "Enhancement of THz Photomixing Efficiency by Using a Pulse-Modulated Multimode Laser Diode", IEEE, 2007, 2 Pgs.
Sims et al., "Relationships Between Leaf Pigment Content and Spectral Reflectance Across a Wide Range of Species, Leaf Structures and Developmental Stages", Remote Sensing of Environment, vol. 81, Jan. 12, 2002, pp. 337-354, doi: https://doi.org/10.1016/S0034-4257(02)00010-X.
Stevens et al., "Global Health Risks: Progress and Challenges", Bulletin of the World Health Organization, vol. 87, 2009, 3 Pgs, doi: 10.2471/BLT.09.070565.
Sukhotin et al., "Photomixing and Photoconductor Measurements on ErAs/InGaAs at 1.55 um", Applied Physics Letters, vol. 82, No. 18, May 5, 2003, pp. 3116-3118, doi: 10.1063/1.1567459.
Sun et al., "A Promising Diagnostic Method: Terahertz Pulsed Imaging and Spectroscopy", World Journal of Radiology, vol. 3, No. 3, Mar. 28, 2011, pp. 55-65, doi: 10.4329/wjr.v3.i3.55.
Sun et al., "Room Temperature GaN/AlGaN Self-Mixing Terahertz Detector Enhanced by Resonant Antennas", Applied Physics Letters, vol. 98, No. 25, Jun. 20, 2011, pp. 252103-1-252103-3, doi: 10.1063/1.3601489.
Suzuki et al., "Fe-Implanted InGaAs Terahertz Emitters for 1.56 um Wavelength Excitation", Applied Physics Letters, vol. 86, Jan. 27, 2005, pp. 051104-1-051104-3, doi: 10.1063/1.1861495.
Takayanagi et al., "High-Resolution Time-of-Flight Terahertz Tomography Using a Femtosecond Fiber Laser", Optics Express, vol. 17, No. 9, Apr. 27, 2009, pp. 7549-7555, doi: https://doi.org/10.1364/OE.17.007533.
Takazato et al., "Detection of Terahertz Waves Using Low-Temperature- Grown InGaAs with 1.56 um Pulse Excitation", Applied Physics Letters, vol. 90, Mar. 9, 2007, p. 101119-1-1011119-3, doi: 10.1063/1.2712503.
Tani et al., "Detection of Terahertz Radiation with Low-Temperature-Grown GaAs-Based Photoconductive Antenna Using 1.55 um Probe", Applied Physics Letters, vol. 77, No. 9, Aug. 28, 2000, pp. 1396-1398, doi: https://doi.org/10.1063/1.1289914.
Tanigawa et al., "Enhanced Responsivity in a Novel AlGaN/GaN Plasmon- Resonant Terahertz Detector Using Gate-Dipole Antenna with Parasitic Elements", IEEE, 2010, pp. 167-168.
Taylor et al., "Resonant-Optical-Cavity Photoconductive Switch with 0.5% Conversion Efficiency and 1.0 W Peak Power", Optics Letters, vol. 31, No. 11, Jun. 1, 2006, pp. 1729-1731.
Thrane et al., "THz Reflection Spectroscopy of Liquid Water", Chemical Physics Letters, vol. 240, Jun. 30, 1995, pp. 330-333.
Tonouchi, Masayoshi "Cutting-Edge Terahertz Technology", Nature Photonics, vol. 1, Feb. 2007, pp. 97-105, doi: 10.1038/nphoton.2007.3.
Trueba et al., "Thresholds for Leaf Damage Due to Dehydration: Declines of Hydraulic Function, Stomatal Conductance and Cellular Integrity Precede those for Photochemistry", New Phytologist, vol. 223, Feb. 18, 2019, pp. 134-149, doi: 10.1111/nph. 15779.

(56) References Cited

OTHER PUBLICATIONS

Tsuda et al., "Application of Plasmon-Resonant Microchip Emitters to Broadband Terahertz Spectroscopic Measurement", Journal of the Optical Society of America B, vol. 26, No. 9, Sep. 2009, p. A52-A57.
Tucker, Compton J. "Remote Sensing of Leaf Water Content in the Near Infrared", Remote Sensing of Environment, vol. 10, 1980, pp. 23-32, doi: https://doi.org/10.1016/0034-4257(80)90096-6.
Turan et al., "Impact of the Metal Adhesion Layer on the Radiation Power of Plasmonic Photoconductive Terahertz Sources", Journal of Infrared, Millimeter, and Terahertz Waves, vol. 38, Aug. 28, 2017, pp. 1448-1456, doi: 10.1007/s10762-017-0431-9.
Ueno et al., "Quantitative Measurements of Amino Acids by Terahertz Time- Domain Transmission Spectroscopy", Analytical Chemistry, vol. 78, No. 15, Aug. 1, 2006, pp. 5424-5428, doi: https://doi.org/10.1021/ac060520y.
Utkin et al., "Adaptive Sliding Mode Control with Application to Super-Twist Algorithm: Equivalent Control Method", Automatica, vol. 49, 2013, pp. 39-47.
Wacoo et al., "Methods for Detection of Aflatoxins in Agricultural Food Crops", Journal of Applied Chemistry, vol. 2014, No. 706291, Nov. 13, 2014, pp. 1-15. doi: https://dx.doi.org/10.1155/2014/706291.
Wallace et al., "Terahertz Pulsed Imaging and Spectroscopy for Biomedical and Pharmaceutical Applications", Faraday Discussions, vol. 126, 2004, pp. 255-263, doi: 10.1039/b309357n.
Wallace et al., "Three-Dimensional Imaging of Optically Opaque Materials Using Nonionizing Terahertz Radiation", Journal of the Optical Society of America A, vol. 25, No. 12, Dec. 2008, pp. 3120-3133, doi: https://doi.org/10.1364/JOSAA.25.003120.
Wang et al., "Noise Analysis of Photoconductive Terahertz Detectors", Journal of Infrared, Millimeter, and Terahertz Waves, vol. 34, Jul. 11, 2013, pp. 519-528, doi: 10.1007/s10762-013-9995-1.
Wang et al., "Plasmonic Photoconductive Detectors for Enhanced Terahertz Detection Sensitivity", Optics Express, 2013, 7 Pgs.
Wang et al., "Terahertz Imaging Applications in Agriculture and Food Engineering: A Review", Transactions of the ASABE, vol. 61, No. 2, 2018, pp. 411-424, doi: https://doi.org/10.13031/trans.12201.
Williams et al., "Human Aflatoxicosis in Developing Countries: A Review of Toxicology, Exposure, Potential Health Consequences, and Interventions", The American Journal of Clinical Nutrition, vol. 80, 2004, pp. 1106-1122, doi: 10.1093/ajcn/80.5.1106.
Unknown Author, "IARC Monographs on the Evaluation of Carcinogenic Risks to Humans: Re-Evaluation of Some Organic Chemicals, Hydrazine and Hydrogen Peroxide", World Health Organization, International Agency for Research on Cancer, vol. 71, 1999, 1597 Pgs (presented in 9 parts).
Yang et al., "7.5% Optical-to-Terahertz Conversion Efficiency Offered by Photoconductive Emitters with Three-Dimensional Plasmonic Contact Electrodes", IEEE Transactions on Terahertz Science and Technology, vol. 4, No. 5, Sep. 2014, pp. 575-581, doi: 10.1109/TTHZ.2014.2342505.
Yang et al., "Enhanced Light-Matter Interaction at Nanoscale by Utilizing High-Aspect-Ratio Metallic Gratings", Optics Letters, vol. 38, No. 18, Sep. 15, 2013, pp. 3677-3679, doi: http://dx.doi.org/10.1364/OL.38.003677.
Yang et al., "Frequency-Tunable Continuous-Wave Terahertz Sources Based on GaAs Plasmonic Photomixers", Applied Physics Letters, vol. 107, 2015, p. 131111-1-131111-4, doi: http://dx.doi.org/10.1063/1.4932114.
Yang et al., "Measurement of the Transmission of the Atmosphere from 0.2 to 2 THz", Optic Express, vol. 19, No. 9, Apr. 25, 2011, pp. 8830-8838.
Yang et al., "Tunable Terahertz Wave Generation Through a Bimodal Laser Diode and Plasmonic Photomixer", Optics Express, vol. 23, No. 24, Nov. 30, 2015, pp. 31206-31215, doi: 10.1364/OE.23.031206.
Yardimci et al., "A High-Power Broadband Terahertz Source Enabled by Three-Dimensional Light Confinement in a Plasomic Nanocavity", Scientific Reports, vol. 7, No. 4166, Jun. 23, 2017, pp. 1-8, doi: 10.1038/s41598-017-04553-4.
Yardimci et al., "A High-Responsivity and Broadband Photoconductive Terahertz Detector Based on a Plasmonic Nanocavity", Applied Physics Letters, vol. 113, Dec. 18, 2018, 251102-1-251102-4, doi: https://doi.org/10.1063/1.5066243.
Yardimci et al., "High Sensitivity Terahertz Detection through Large-Area Plasmonic Nano-Antenna Arrays", Scientific Reports, vol. 7, No. 42667, Feb. 16, 2017, pp. 1-8, doi: 10.1038/srep42667.
Yardimci et al., "High-Power Terahertz Generation Using Large-Area Plasmonic Photoconductive Emitters", IEEE Transactions on Terahertz Science and Technology, vol. 5, No. 2, Mar. 2015, pp. 223-229, doi: 10.1109/TTHZ.2015.2395417.
Extended European Search Report for European Application No. 20883093.5, dated Oct. 13, 2023, dated Oct. 26, 2023, 25 Pgs.
Li et al., "Monitoring Soybean Leaf Water Status using Terahertz Spectroscopy", 2018 43rd International Conference on Infrared, Millimeter, and Terahertz Waves(IRMMW-THZ), IEEE, Sep. 9, 2018 (Sep. 9, 2018), p. 1, XP033430718, DOI: 10.1109/IRMMW-THZ.2018.8510251.
Singh et al., "Terahertz 3D Water Distribution in Plant Leaves", 44th International Conference on Infrared, Millimeter, and Terahertz Waves (IRMMW-THZ), IEEE, Sep. 1, 2019 (Sep. 1, 2019), pp. 1-2, XP033636539, DOI: 10.1109/IRMMW-THZ.2019.8873718.
Song et al., "Temporal and Spatial Variability of Water Status in Plant Leaves by Terahertz Imaging", IEEE Transactions on Terahertz Science and Technology, IEEE, Piscataway, NJ, USA, Sep. 1, 2018 (Sep. 1, 2018), vol. 8, No. 5, pp. 520-527, XP011689856, DOI: 10.1109/TTHZ.2018.2851922.
Xing et al., "Nondestructive examination of polymethacrylimide composite structures with terahertz time-domain spectroscopy", Polymer Testing, vol. 57, pp. 141-148, XP029857453, DOI: 10.1016/J.POLYMERTESTING.2016.11.022.

* cited by examiner

METHOD FOR IDENTIFYING CHEMICAL AND STRUCTURAL VARIATIONS THROUGH TERAHERTZ TIME-DOMAIN SPECTROSCOPY

CROSS REFERENCE TO RELATED APPLICATIONS

This application is a national stage of PCT Patent Application No. PCT/US20/53860, entitled "Method for Identifying Chemical and Structural Variations Through Terahertz Time-Domain Spectroscopy" to Jarrahi et al., filed Oct. 1, 2020, which claims priority to U.S. Provisional Application No. 62/909,038, entitled "Method for Detecting Aflatoxins and Other Hazardous Mycotoxins in Agricultural Food Products through Terahertz Time-Domain Spectroscopy" to Jarrahi et al., filed Oct. 1, 2019, the disclosures of which are incorporated by reference herein in their entirety.

FIELD OF THE INVENTION

The current disclosure is directed to systems and methods for direct, high-sensitivity, high-throughput, and non-invasive detection of hazardous mycotoxins, including aflatoxins, in agricultural food products via terahertz time-domain spectroscopy.

BACKGROUND OF THE INVENTION

Terahertz radiation consists of electromagnetic waves within the band covering roughly the electromagnetic spectrum from 0.1 to 10 THz. Accordingly, terahertz radiation occupies a middle ground between microwaves and infrared light waves known as the "terahertz gap." Since many resonances, such as internal rotational of light hydrides, rotational-vibrational bending of carbon-chain molecules, and intramolecular vibrations of inorganic molecules, happen at terahertz frequencies, terahertz band contains spectral lines of many organic and inorganic molecules. Furthermore, unlike infrared or visible waves, terahertz waves can penetrate through many optically-opaque media and, thus, they can interact with a substrate hidden below the surface of a sample. As such, terahertz waves can also propagate through most of the packaging materials, such as plastic, paper, cardboard, and foam, which makes terahertz waves very suitable for evaluation of, for example, packaged foods. Moreover, terahertz photons have very low energy compared to X-rays and don't pose any health hazard. However, despite many advantageous characteristics, the use of terahertz waves has never been found practical for applications outside of laboratory setting.

SUMMARY OF THE INVENTION

Many embodiments are directed to systems and methods for direct, high-sensitivity, high-throughput, and non-invasive detection of hazardous mycotoxins, including aflatoxins, in agricultural food products via terahertz time-domain spectroscopy.

Various embodiments are directed to a method for identifying chemical and structural irregularities in a substrate, comprising:
providing a sample comprising a plurality of points and having chemical or structural variations;
providing a terahertz scanner comprising:
 at least one terahertz source generating a terahertz beam travelling along a terahertz beam path, and
 at least one terahertz detector, wherein
 the terahertz scanner produces a characteristic signal when the terahertz beam is detected by the at least one terahertz detector after interacting with a point of the plurality of points of the sample; and
 the terahertz scanner produces a reference signal when the terahertz beam is not intercepted by the sample;
obtaining a characteristic and a reference signals for at least one point of the plurality of points of the sample;
extracting characteristic features from characteristic data afforded by the characteristic signal, and extracting corresponding reference features from reference data afforded by the reference signal; wherein at least one of the characteristic and the corresponding reference features are selected from the list consisting of: peak intensity, average intensity, delay, pulse width, spectral power, phase of the signals, and any combination thereof;
analyzing the characteristic and the corresponding reference features using a machine learning data analysis model to find chemical and or structural information about the sample; and
recognizing irregularities in or differences between the characteristic and the corresponding reference features to identify the chemical or structural variations in the sample.

In various such embodiments, the machine learning data analysis model is selected from the list consisting of: supervised model, unsupervised model, and any combination thereof.

In still various such embodiments, the machine learning data analysis model is trained to recognize the chemical or structural variations in the sample.

In yet various such embodiments, the terahertz scanner is a terahertz time-domain spectroscopy scanner.

In still yet various such embodiments, wherein the terahertz scanner is a terahertz time-domain spectroscopy scanner, the terahertz scanner further comprises:
 a femtosecond laser generating an optical beam, and
 a plurality of optical lenses for focusing the optical beam along an optical beam path.

In various such embodiments, wherein the terahertz scanner is a terahertz time-domain spectroscopy scanner, the terahertz scanner further comprises a plurality of terahertz lenses and or off-axis parabolic mirrors for focusing and or collimating the terahertz beam along the terahertz beam path.

In still various such embodiments, wherein the terahertz scanner is a terahertz time-domain spectroscopy scanner, the characteristic signal and the reference signal are in time domain.

In yet still various such embodiments, wherein the terahertz scanner is a terahertz time-domain spectroscopy scanner, the characteristic signal and the reference signal in time domain are used to find their corresponding signals in frequency-domain; and extracting the characteristic features and the corresponding references features in both time domain and frequency domain.

In various such embodiments, the chemical or structural variations are selected from the list consisting of: chemical contamination, material defects, other irregularities in a material, and any combination thereof.

In still various such embodiments, the chemical contamination comprises a toxin.

In yet various such embodiments, the toxin is selected from the group consisting of: any type of mycotoxins, any type of aflatoxins, or a combination thereof.

In still yet various such embodiments, the material defects are further selected from the list consisting of: thickness variations, voids, cracks, non-uniformities, and any combination thereof.

In yet still various such embodiments, the sample comprises a battery electrode and the chemical or structural variations are material defects.

In still various such embodiments, the sample comprises a composite material and the chemical or structural variations are material defects.

In yet still various such embodiments, wherein the terahertz scanner comprises the femtosecond laser, the femtosecond laser is selected from: a single femtosecond laser combined with a delay stage, a dual femtosecond laser.

In still yet various such embodiments, wherein the terahertz scanner comprises the femtosecond laser, the femtosecond laser is generating optical beam at a wavelength selected from: ~800 nm, 1550 nm.

In various such embodiments, wherein the terahertz scanner comprises the plurality of optical lenses, the plurality of optical lenses adjusts the spot size of the optical beam to cover the active area of the terahertz source and the terahertz detector.

In still various such embodiments, the at least one terahertz detector is selected from a list consisting of: a single-pixel terahertz detector, a focal plane 1D or 2D array comprising a plurality of terahertz detectors.

In yet various such embodiments, the at least one terahertz detector is capable of taking three-dimensional terahertz snapshots of an area as large as ~10 cm$^2$ within less than a 100 ms.

In still yet various such embodiments, the at least one terahertz source and the at least one terahertz detector comprise plasmonic electrodes.

In various such embodiments, wherein the at least one terahertz source and the at least one terahertz detector comprise plasmonic electrodes, the at least one terahertz source and the at least one terahertz detector are fabricated on a semiconductor substrate and optimized for operation at 800 nm or 1550 nm wavelengths.

In yet various such embodiments, wherein the at least one terahertz source and the at least one terahertz detector comprise plasmonic electrodes, the terahertz source and the terahertz detector are fabricated on a GaAs, InGaAs and InAs substrate.

In still various such embodiments, wherein the terahertz scanner comprises the comprises the plurality of terahertz lenses and or off-axis parabolic mirrors, the plurality of terahertz lenses is made from a material selected from: polyethylene, TPX, ceramic, Teflon, and any combination thereof.

In yet still various such embodiments, the sample is placed on a sample holder selected from: a moving conveyor belt, a single or multi-well plate or multiple plates mounted on a motorized translational stage, and any combination thereof.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures, which are presented as exemplary embodiments of the invention and should not be construed as a complete recitation of the scope of the invention, wherein:

FIGS. 2A through 2E illustrate various aspects of an enhanced plasmonic terahertz source/detector for use in the terahertz imaging scanners, wherein FIG. 2A shows a schematic diagram and operation concept for the enhanced plasmonic terahertz source/detector; FIG. 2B shows top view scanning electron microscope (SEM) images of the enhanced plasmonic terahertz source/detector optimized for operation at 800 nm optical pump/probe wavelength; while FIGS. 2C, 2D, and 2E, respectively illustrate radiated power, time-domain radiated field, and frequency-domain radiated power that can be obtained from the enhanced plasmonic terahertz source, in accordance with prior art.

FIG. 6B provides an example of raw data collected for an arbitrary point on a tested almond.

FIG. 7B provides the resulting absorption parameters calculated for a variety of healthy samples and samples contaminated with different types of aflatoxins as a function of aflatoxin concentration; and FIGS. 7C and 7D provide flowcharts explaining the data training and data processing employed with the algorithm to achieve quantitative mycotoxins detection in accordance with embodiments of the invention.

FIGS. 11A through 11D provide X-ray CT images of a commercial NCM cathode on an Al current collector featuring various defects, wherein FIG. 11A shows a cross-section thickness variation defect; FIG. 11B shows in-plane cracks and holes defects; FIG. 11C provides an in-plane higher resolution image showing a defect in Al foil bending with 10 µm bend roughness; and FIG. 11D shows volume-rendered cathode electrode at higher resolution—all according to prior art.

FIGS. 12A through 12E illustrate THz imaging methods in accordance prior art, wherein FIG. 12A is a 3D image of a LIB anode electrode afforded by one of the conventional THz systems and methods; FIGS. 12B and 12C, respectively, provide X-Z and Y-Z cross-sectional images obtained from further processed 3D THz image of FIG. 12A, and FIGS. 12D and 12E show C-scan images of, respectively, the graphite and metal surfaces obtained by windowing the deconvolved time-domain signal from the LIB anode electrode.

DETAILED DESCRIPTION OF THE INVENTION

Figure 1:
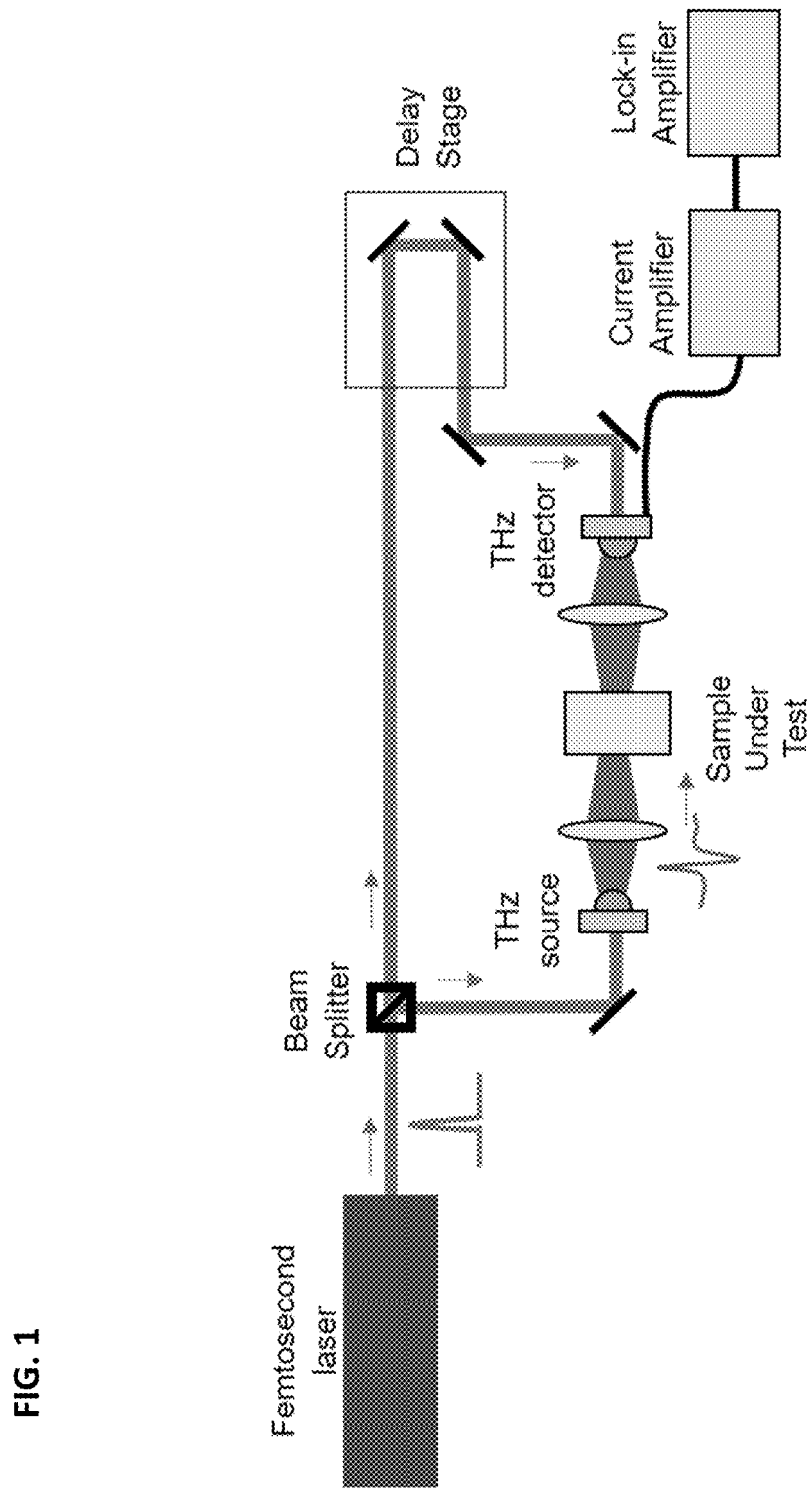
FIG. 1 provides a schematic for an example of a terahertz time-domain spectroscopy (THz-TDS) scanner, in accordance with embodiments of the invention.

Turning to the drawings and data, descriptions of apparatuses and methods for detecting chemical contaminations, material defects or irregularities, and or material damage in a sample through terahertz time-domain spectroscopy in real time with high sensitivity and throughput are provided. It will be understood that the embodiments of the invention described herein are not intended to be exhaustive or to limit the invention to precise forms disclosed. Rather, the embodiments selected for description have been chosen to enable one skilled in the art to practice the invention.

Terahertz (THz) radiation has many unique specifications which, in principle, make it a good candidate for non-destructive quality control applications, such as detection of chemical contaminants, other irregularities, and or damage in a substrate. For example, the photon energy at terahertz frequencies is very low and, therefore, terahertz waves do not pose any hazard to human health or the sample being analyzed. In addition, terahertz waves can penetrate through many non-metallic materials, allowing to probe a substance underneath many common packaging or coating materials. However, despite the great promises of terahertz radiation-based technologies, including for non-invasive high-throughput detection applications, the utilization of terahertz waves in practical settings has not been realized to date, due to the low sensitivity and resolution of available terahertz scanners, which suffer from low Signal to Noise Ratio (SNR) levels, as well as primitive data analysis techniques adopted for such applications. More specifically, conventional terahertz imaging systems and methods cannot offer high resolution due to the diffraction limit, wherein 1 THz corresponds to 300 µm wavelength, which means that even a terahertz imaging system with the perfect configuration can offer only hundreds of micrometers of resolution. In fact, even reaching a resolution at the Abbe's diffraction limit is not usually possible due to the limitations of terahertz optical components. For example, even the state-of-the-art terahertz scanner systems generally offer 1-3 mm spatial resolution (Terahertz Gauging and Imaging products by Luna: https://lunainc.com/product-category/sensing-and-non-destructive-test-products#category-15; and terahertz imaging scanner by TeraSense: https://terasense.com/products/thz-scanner/, the disclosures of which is incorporated herein by reference), which clearly excludes terahertz wave-based technologies from many applications, such as, for example, analysis of defects in battery electrodes, such as, for example, electrodes in lithium-ion batteries (LIBs), due to small size of the electrodes.

Furthermore, in order to be useful for detection of chemical contaminants and material defects, a THz imaging system need to have a large SNR to obtain output data that is sufficiently accurate for analysis, despite attenuation of terahertz pulses propagating through the sample. One possible solution to reducing the system's noise is increasing the number of taken measurements and averaging such measurements. However, such approach results in the slowing of sample evaluation and decreasing the scanning throughput. Accordingly, one demonstrated approach to overcoming the SNR issues is to use more powerful terahertz sources and more sensitive terahertz detectors (Berry, C. W., et al., 2013, Significant performance enhancement in photoconductive terahertz optoelectronics by incorporating plasmonic contact electrodes, Nature communications, 4, 1622; Yardimci, N. T., et al., 2015, High-power terahertz generation using large-area plasmonic photoconductive emitters, IEEE Transactions on Terahertz Science and Technology, 5(2), 223-229; and Yardimci, N. T., et al., 2017, High sensitivity terahertz detection through large-area plasmonic nano-antenna arrays, Scientific reports, 7, 42667, the disclosure of which are incorporated herein by reference).

In addition, in order to improve the speed and sensitivity of the detection of irregularities with THz technologies, it is necessary to have a robust algorithm for evaluation of the measurement results. Moreover, a robust algorithm is also needed to address the challenges associated with the sample preparation, wherein meticulous sample preparation procedures are often necessary for the successful identification and quantitation of irregularities, especially chemical contaminants, by all currently used THz spectroscopy imaging methods (Grischkowsky, D., et al., 1990, Far-infrared time-domain spectroscopy with terahertz beams of dielectrics and semiconductors, JOSA B, 7(10), 2006-2015; Zhang, X., et al., 2017, Simultaneous determination of amino acid mixtures in cereal by using terahertz time domain spectroscopy and chemometrics, Chemometrics and Intelligent Laboratory Systems, 164, 8-15; Parrott, E. P. J., et al., 2011, Terahertz spectroscopy: Its future role in medical diagnoses, Journal of Molecular Structure, 1006(1-3), 66-76; Ge, H., et al., 2016, Quantitative determination of aflatoxin $B_1$ concentration in acetonitrile by chemometric methods using terahertz spectroscopy, Food chemistry, 209, 286-292; and Chen, M., et al., 2014, A preliminary study of aflatoxin $B_1$ detection in peanut oil by terahertz time-domain spectroscopy, Transactions of the ASABE, 57(6), 1793-1799, the disclosure of which are incorporated herein by reference). As one stark example, all of the studies to date that have investigated hazardous toxin aflatoxin detection in agricultural produce by THz spectroscopy have relied on data analysis algorithms requiring preparation of uniform samples with planar surfaces, which does not allow for high-throughput detection and is not practical for field settings. Accordingly, although these laboratory experiments did confirm that aflatoxins have unique spectral signatures in the terahertz band, they also suggested that terahertz spectroscopy could not be successfully used with solid agricultural products of arbitrary shapes. Therefore, in order to employ THz techniques in realistic settings with high throughput, robust algorithms are needed, wherein such algorithms could eliminate geometry dependence of the terahertz measurements and calculate thickness- and shape-independent absorption parameter corresponding to the sought after detection output, thus allowing for identification and or quantification of the studied irregularity or irregularities in any sample or substrate with high sensitivity and high throughput without any special sample preparation.

This application is directed to embodiments of high-throughput, contactless, non-invasive, yet highly-sensitive methods and scanners for detection of various types of irregularities, such as chemical and or structural variations, in a substrate using terahertz wave radiation. In some embodiments, the irregularities are chemical variations, such as, for example, chemical contaminants, including hazardous toxins. In many such embodiments, the substrate includes produce, such as, for example, agricultural produce. In some embodiments, the hazardous toxins are mycotoxins, including all types of aflatoxins. In some embodiments, the irregularities are structural variations, such as, for example, microscale defects or damage in man-made materials, such as, for example, composite materials and electrodes, including LIB electrodes. In many embodiments, the methods and scanners for the detection of irregularities address and overcome many limitations of the conventional terahertz scanning systems. For example, in many embodiments the methods and scanners of the application do not require special sample preparation or a skilled operator. In many embodiments, the methods of the application rely on pulsed terahertz imaging scanners based on a system such as schematically depicted in FIG. 1, provided herein as an example, wherein the system at least comprises a terahertz source and a terahertz detector. In many such embodiments, the THz source and the THz detector are plasmonic. In many embodiments, the use of the THz source and the THz detector enhanced with plasmonic technology offers several orders of magnitude higher SNR levels, as compared to conventional terahertz source and detector technologies. In many embodiments, the THz detector comprises a focal plane array, which consists of a single plasmonic terahertz detector or a 2D array of plasmonic terahertz detectors.

In many embodiments, the methods for the detection of irregularities in a substrate or sample rely on advanced terahertz imaging algorithms described herein. In many embodiments, especially wherein the irregularities are chemical contaminants, the algorithms of the instant disclosure are capable of direct calculation of the contaminants' concentration in the sample, in addition to identifying the contaminants. In many embodiments, especially wherein the irregularities are substrate material irregularities or defects, the algorithms of the instant disclosure allow for direct imaging of the irregularities or defects. In many embodiments, the algorithms of the instant disclosure rely on various terahertz parameters extracted from the data collected by measuring terahertz pulses transmitted and reflected from the examined samples/substrates. More specifically, in many embodiments, the algorithms extract one or more various features from the THz signal that has interacted with the sample being analyzed, and compare the extracted feature or features to the corresponding feature or features extracted from a reference THz signal. In many embodiments, the signal features include one or more features selected from the list comprising (but not limited to): time-domain peak field, time domain delay, time-domain pulse width, frequency-domain spectral power, frequency-domain phase, or any combination thereof, or another feature or features. For example, in some embodiments, the algorithm may rely on measurements of the intensity and delay of the terahertz pulses transmitted and reflected from examined samples. In many embodiments, the algorithms of the instant disclosure feed the extracted features to a machine learning data analysis model, such as, for example, a neural network, or a dense neural network, to obtain the desired information regarding the identity of the contamination (or another irregularity) in a sample and or its amount. In some embodiments, first, the algorithms may feed the machine learning data analysis model the extracted features obtained from the THz analysis of samples with known and well-defined contamination (or other defect or irregularity) to train the machine learning data analysis model, prior to using the machine learning data analysis model for the analysis of the desired substrates/samples.

Terahertz Imaging Scanner

FIG. 1 schematically illustrates the terahertz imaging scanner designed according to many embodiments for detection of irregularities in a substrate. In many embodiments, the terahertz scanners comprise at least a terahertz source generating a terahertz beam and a terahertz detector. In many embodiments, the terahertz scanners further comprise: a plurality of terahertz lenses and or off-axis parabolic mirrors for focusing and or collimating the terahertz beam along a terahertz beam path, a femtosecond laser generating an optical beam, a plurality of optical lenses for focusing the optical beam along an optical beam path, and a sample surface or sample holder disposed on the terahertz beam path. In some embodiments, the THz scanner also comprises an optional ejection arm for removal of undesirable samples from the sample surface. In many embodiments, a sample to be analyzed for contamination or other irregularities or defects is disposed on the sample surface or inside the sample holder, such as, for example, a sample well. In some embodiments, the terahertz source and the terahertz detector or detectors are plasmonic. In some embodiments, the terahertz detector is selected from: a single-pixel terahertz detector, a focal plane 2D array of a plurality of terahertz detectors. In many embodiments, wherein the terahertz detector is a 2D array of a plurality of terahertz detectors, the image acquisition rate of the scanners of embodiments is significantly increased due to the lateral sample scan time reduction, enabling high-throughput detection of mycotoxins in real-time. In many embodiments, the femtosecond laser is one of: a single femtosecond laser combined with a delay stage, or a dual femtosecond laser. In many embodiments, the terahertz detector is pumped/probed by femtosecond optical beams from a phase-modulated dual-laser-synchronized control femtosecond laser. In some embodiments, the femtosecond laser is characterized by $\lambda \sim 1550$ nm, which is the fiber-optic communication wavelengths. In some embodiments, it is advantageous to operate at the wavelength of 1550 because low dispersion, polarization maintaining, optical fibers are available for this wavelength for maintaining the pulse width and polarization of the femtosecond pump beams over a fiber length of several meters. Consequently, operating at the wavelength of 1550 enables the development of compact and light-weight imaging systems for practical quality control applications in field settings. In many embodiments, the terahertz imaging scanner is handheld. However, in many embodiments, the selection of the optical wavelength used in detection of irregularities in a substrate may be based on the availability of a laser system, and other relevant components. In addition, in many embodiments, the spot size of the optical pump/probe beams is adjusted by a plurality of lenses to cover the active area of the plasmonic terahertz source and the terahertz detector/focal plane array. In some such embodiments, the plasmonic terahertz source and/or the plasmonic terahertz detector are mounted on a silicon lens, and the terahertz lenses and/or off-axis parabolic mirrors are used to collimate or focus the radiated terahertz beam. In many embodiments, the terahertz lens is made from a material selected from: polyethylene, polymethylpentene (TPX), ceramic, Teflon. In many embodiments, the sample surface is a moving conveyor belt. In many embodiments, the sample surface or holder comprises plastic.

In many embodiments, an irregularity detection measurement is obtained when a terahertz beam radiated from the terahertz source illuminates a sample, gets transmitted (or reflected) by that sample, and, in turn, is focused on the terahertz detector/focal plane array located past the sample on the terahertz beam path by use of terahertz lenses and/or off-axis parabolic mirrors lens. More specifically, in many embodiments, a measurement signal is obtained by, for example, having a femtosecond laser generate a near IR optical pulse train, wherein some portion of these pulses are used to pump a terahertz source to generate pulsed terahertz radiation. Next, the generated pulsed radiation is guided and focused on the substrate being tested for irregularities, which transmits or reflects the THz beam. Next, the transmitted or reflected by the substrate terahertz radiation is re-focused on the terahertz detector probed by the other portion of the femtosecond optical pulse train. The interaction between the terahertz and optical pulses in the photoconductive terahertz detector induces an ultrafast photocurrent if the pulses are incident on the terahertz detector simultaneously. The time synchronization of the terahertz and optical probe pulses is usually controlled by an optical delay line. By changing the delay between these two pulses, the ultrafast photocurrent can be sampled. This photocurrent carries information about the substrate under the test, since it has a direct relation with the incident terahertz pulse, which, in turn, interacts with the substrate before reaching the detector. Hence, it is possible to extract structural information about the substrate by analyzing the induced photocurrent. In many such embodiments, the output from the terahertz detector or focal plane array is synthesized into a pulse amplitude and, for example, a pulse delay image using the algorithm of the instant disclosure. In many embodiments, 15×15 amplitude/delay images of the sample are captured in less than 10 ms with a 60 dB SNR per pixel. In many embodiments, increasing the pixel size to 100×100 decreases the SNR per pixel to 40 dB over a 10 ms scan time, while still maintaining adequate sensitivity towards irregularities, such as, for example, chemical contaminants.

Enhanced Plasmonic Terahertz Sources and Detectors

In some embodiments, an enhanced plasmonic terahertz source and detector technology is utilized in the terahertz imaging scanners of the instant application and offer orders of magnitude higher SNR levels, as compared to the conventional photoconductive terahertz sources and detectors (see: Berry, C. W., et al., 2014, Generation of high power pulsed terahertz radiation using a plasmonic photoconductive emitter array with logarithmic spiral antennas, Applied Physics Letters, 104(8), 081122; Berry, C. W., et al., 2014, High power terahertz generation using 1550 nm plasmonic photomixers, Applied Physics Letters, 105(1), 011121; Berry, C. W., et al., 2014, Plasmonics enhanced photomixing for generating quasi-continuous-wave frequency-tunable terahertz radiation, Optics letters, 39(15), 4522-4524; Yang, S. H., et al., 2014, 7.5% optical-to-terahertz conversion efficiency offered by photoconductive emitters with three-dimensional plasmonic contact electrodes, IEEE Transactions on Terahertz Science and Technology, 4(5), 575-581; Berry, C. W., et al., 2012, Terahertz generation using plasmonic photoconductive gratings, New Journal of Physics, 14(10), 105029; Jarrahi, M., 2015, Advanced photoconductive terahertz optoelectronics based on nano-antennas and nano-plasmonic light concentrators, IEEE Transactions on Terahertz Science and Technology, 5(3), 391-397; Yang, S. H., et al., 2015, Frequency-tunable continuous-wave terahertz sources based on GaAs plasmonic photomixers, Applied Physics Letters, 107(13), 131111; S.-H. Yang, et al., 2015, Tunable terahertz wave generation through a bimodal laser diode and plasmonic photomixer, Optics Express, 23(24), 31206-31215; Li, X., et al., 2017, A polarization-insensitive plasmonic photoconductive terahertz emitter. AIP advances, 7(11), 115113; Turan, D., et al., 2017, Impact of the Metal Adhesion Layer on the Radiation Power of Plasmonic Photoconductive Terahertz Sources, Journal of Infrared, Millimeter, and Terahertz Waves, 38(12), 1448-1456; Yardimci, N. T., et al., 2017, A High-Power Broadband Terahertz Source Enabled by Three-Dimensional Light Confinement in a Plasmonic Nanocavity, Scientific reports, 7(1), 4166; Yardimci, N. T., et al., 2018, A high-responsivity and broadband photoconductive terahertz detector based on a plasmonic nanocavity, Applied Physics Letters, 113(25), 251102; Baker, R. D., et al., 2018, Self-triggered Asynchronous Optical Sampling Terahertz Spectroscopy using a Bidirectional Mode-locked Fiber Laser, Scientific Reports, 8, 14802; and Yardimci, N. T., et al., 2018, Nanostructure-Enhanced Photoconductive Terahertz Emission and Detection, Small, 14(44), 1802437, the disclosures of which are incorporated herein by reference). More specifically, in many such embodiments, the designer nanoplasmonic structures incorporated in the active area of the photoconductive terahertz sources and detectors are very effective in significantly enhancing terahertz radiation powers and detection sensitivities and, thus, make for THz scanning systems with very high SNR, and allow to achieve adequate sensitivity levels with smaller number of measurements, enabling shorter scanning times.

Figure 2A:
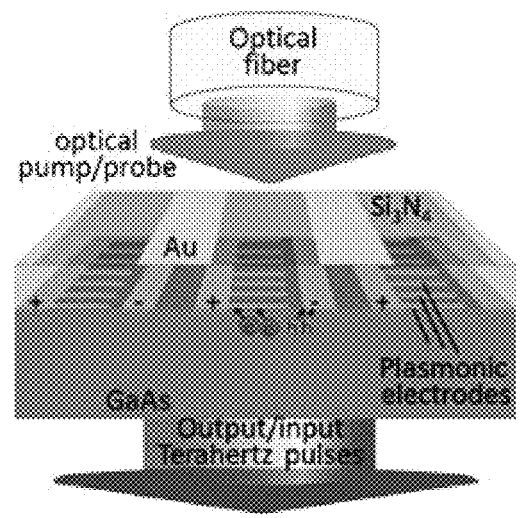

In many such embodiments, the enhanced plasmonic terahertz sources and detectors significantly increase the image depth and data accuracy of existing terahertz imaging systems when used for detection of irregularities in a substrate. FIG. 2A shows a schematic diagram and operation concept for such enhanced plasmonic terahertz source/detector for utilization in the terahertz imaging scanners of the instant application. Specifically, FIG. 2A shows that when the active area of the plasmonic terahertz source is illuminated by an optical pump beam, photo-generated electrons and holes are accelerated in opposite directions by an external bias electric field. Accordingly, the acceleration and separation of the photocarriers induce a time-varying dipole moment within the device active area, which, in turn, generates terahertz radiation. Similarly, when the active area of the plasmonic detector is illuminated by an optical probe beam, photo-generated electrons and holes are accelerated in opposite directions by the received terahertz field reflected from the imaged sample. The acceleration and separation of the photocarriers induce a photocurrent within the device active area which is proportional to the received terahertz field. In addition, to further enhance the terahertz radiation powers of the plasmonic terahertz source and the detection sensitivities of the plasmonic terahertz detector, a key feature of the enhanced source/detector design comprises the use of plasmonic contact electrodes inside the device's active area, such that the majority of the photocarriers are concentrated in the close proximity to the device's contact electrodes to efficiently contribute to terahertz generation and detection. This design feature results in significantly higher terahertz radiation powers and terahertz detection sensitivities, as compared to conventional designs.

Figure 2B:
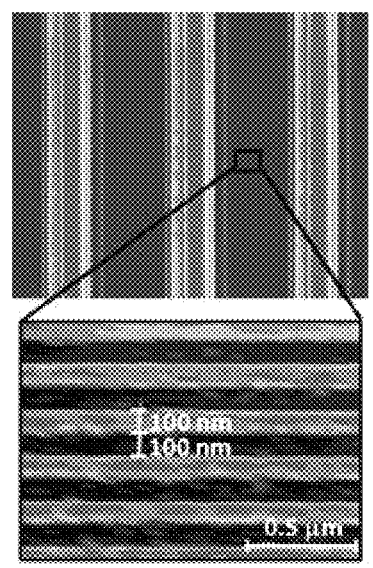
Figure 2C:
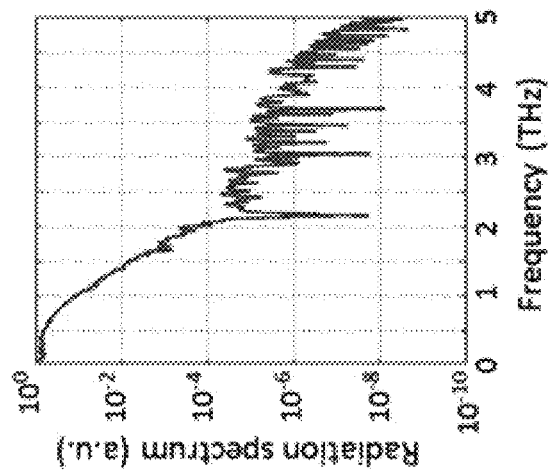
Figure 2D:
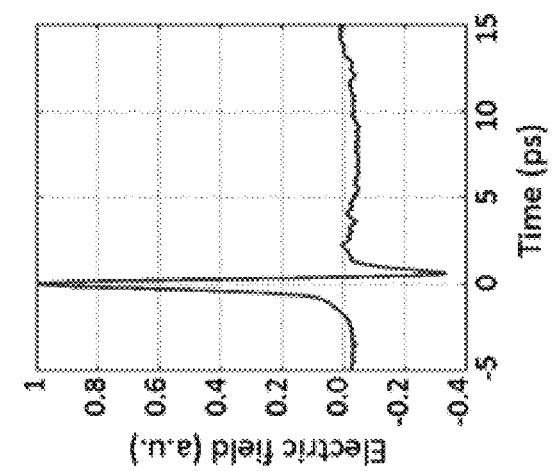
Figure 2E:
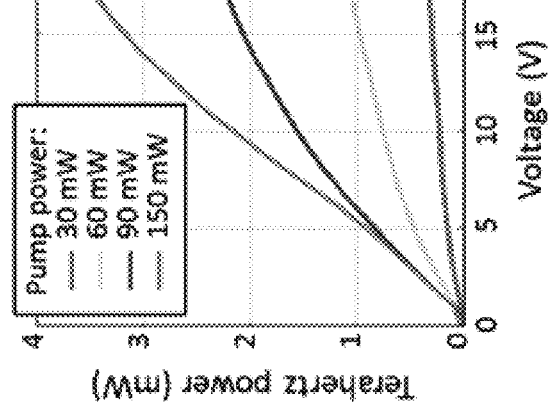

As an example, FIG. 2B shows the scanning electron microscopy (SEM) images of such enhanced plasmonic terahertz source/detector fabricated on a GaAs substrate and optimized for operation at 800 nm optical pump/probe wavelength. As such, the terahertz radiation from this enhanced source is characterized by use of a Ti:sapphire mode-locked laser with a repetition rate of 76 MHz and a pulse width of 200 femtosecond, indicating unprecedently high terahertz radiation powers, as high as 3.6 mW at an optical pump power of 150 mW, and exhibiting two orders of magnitude higher optical-to-terahertz conversion efficiencies, as compared to conventional large area photoconductive terahertz sources (FIG. 2C). In addition, the radiated electric field from the enhanced plasmonic terahertz source is characterized in a time-domain terahertz spectroscopy setup with an enhanced plasmonic terahertz detector. The measured time-domain radiated field and frequency-domain radiated power of the enhanced plasmonic terahertz source at 50 mW optical pump power are shown in FIGS. 2D and 2E, respectively, and exhibit a terahertz radiation pulse width of 0.3 picosecond FWHM and a terahertz radiation spectrum in the 0.1-5.5 terahertz frequency range with more than 120 dB SNR achieved when capturing and averaging 1000 time-domain data traces. In many embodiments, the plasmonic nanoantenna arrays of the instant disclosure can offer record-high radiation power levels and detection sensitivities, as well as large field-of-views that are all critical for high-accuracy, high-throughput operation. The use of the plasmonic THz sources and THz detectors in the terahertz scanner systems of embodiments offers >90 dB SNR over a 0.1-5.5 THz frequency range for a single trace measurement, which can be completed in 1 ms. Compared to the currently available commercial terahertz systems, this SNR value represents more than 25 dB enhancement in SNR for the same measurement time, enabling higher accuracy measurements and faster scanning rates by reducing the requirement for multiple measurements.

In some embodiments, the design and geometry of the enhanced plasmonic terahertz source/detector is optimized for fabrication on an ErAs:InGaAs substrate, in order to operate the detection of irregularities at 1550 nm optical pump/probe wavelengths. This wavelength is preferred in some embodiments because it can be easily accommodated by commercially available low-dispersion fibers, fiber components, and fiber lasers. Furthermore, in many such embodiments, short carrier lifetime of ErAs:InGaAs offers relatively lower noise floors for the plasmonic terahertz sources and detectors, as compared to other photo-absorbing substrates at 1550 nm wavelengths, by reducing the induced low frequency photocurrent. As such, ErAs:InGaAs substrates have been used for plasmonic terahertz sources and detectors and demonstrate highest terahertz radiation powers in continuous-wave operation. In many embodiments, a variety of plasmonic terahertz source/detector geometries and architectures is used to obtain the optimal performance based on the tradeoffs between terahertz radiation power and detection sensitivity relative to the terahertz radiation/detection bandwidth. In many such embodiments, the designs with the highest terahertz radiation power levels, detection sensitivity levels, and terahertz generation/detection bandwidths are selected for integration with the terahertz imaging scanners of the disclosure, in order to maximize the imaging depth, image contrast, and image resolution in the methods of the instant disclosure for detection of irregularities in a substrate.

In some embodiments, wherein the terahertz imaging scanner comprises:
1) the enhanced plasmonic terahertz source/detector design shown in FIGS. 2A-2E, wherein the enhanced plasmonic terahertz source/detector utilizes a modified plasmonic electrode geometry on an ErAs:InGaAs substrate optimized for operation at 1550 nm pump/probe wavelengths, and
2) a phase-modulated dual-femtosecond-laser system, offering 250 mW femtosecond optical pump/probe pulses with 50 fs pulse width and 50 MHz repetition rate;

and wherein the terahertz imaging scanner is characterized by:
a 1×1 mm$^2$ plasmonic terahertz source,
a focal plane array with 15×15 plasmonic terahertz detectors with a 0.2×0.2 mm$^2$ area,
a terahertz radiation power of ~1 mW, and
a radiation pulse width of 0.4 ps, the SNR is 60 dB per pixel (detector). In many embodiments, increasing the size of the focal plane array to 100×100 plasmonic terahertz detectors/pixels leads to a decreased per pixel SNR of 40 dB over a 10 ms scan time, which is still adequate for many detecting applications. For example, such sensitivity is adequate for detection of aflatoxin toxins contamination in agricultural produce, wherein the maximum allowed by the FDA regulation aflatoxin contamination level is 20 ppb.

Data Analysis Algorithm

Figure 3:
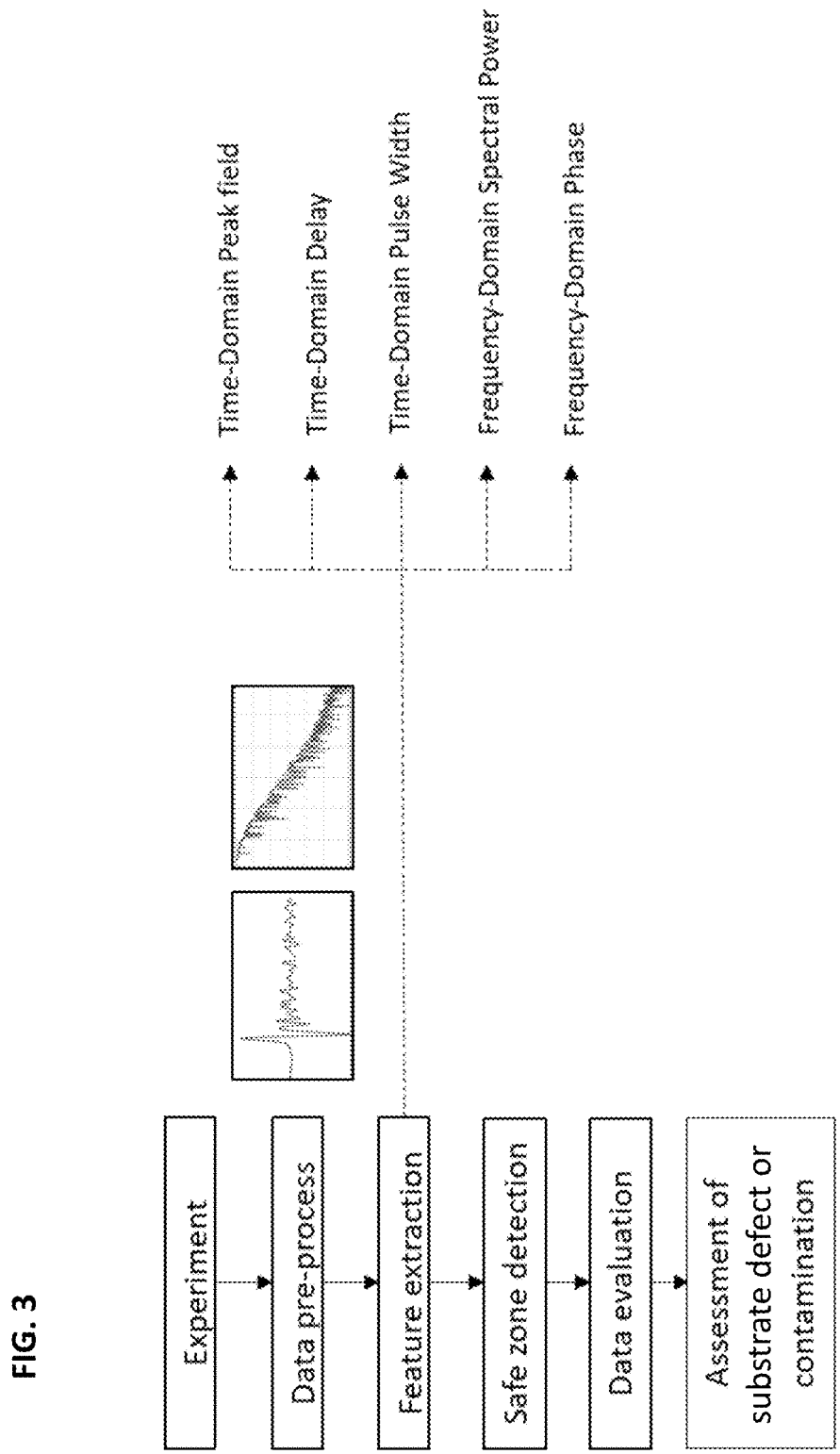
FIG. 3 provides a generalized flowchart describing the data processing and evaluation algorithms employed in the detection of irregularities in a substrate methods in accordance with embodiments of the invention.

In many embodiments, the advanced algorithms of the instant disclosure employ machine learning and are capable of direct identification and, in some embodiments, quantification of irregularities in a substrate. FIG. 3 provides a flowchart describing a general data processing and evaluation algorithm that may be employed with the terahertz imaging scanner of the instant disclosure in the irregularities detection methods according to many embodiments. According to this algorithm and methods, the data collected by the terahertz imaging scanner of embodiments is preprocessed to obtain time-domain and the corresponding frequency-domain signals for each sample point a measurement is taken. Furthermore, various features, such as peak field, delay, pulse width, spectral power, and phase, are extracted from the obtained time-domain and frequency-domain signals. Next, the data processing algorithm of embodiments may use the extracted various features to feed the machine learning data analysis model, such as, for example, a neural network, which is, in turn, trained to predict the identity and or amount of the irregularities in the studied sample.

More specifically, in many embodiments, the data evaluation algorithms of embodiments use a machine learning data analysis model trained to predict irregularities, such as contamination or defects, in samples. In such embodiments, the machine learning data analysis model is fed the various features extracted from the data comprising the time-domain and frequency-domain signals measured at each sample point by the terahertz imaging scanner of embodiments. According to many embodiments, the extracted various features are directly related to the optical properties of the sample being analyzed for the presence of irregularities, wherein the optical properties of the sample are a function of the type of the irregularities and the contamination level. In many embodiments, some of the extracted various features are used to train the machine learning data analysis model, while others are used to evaluate the performance of the machine learning data analysis model by predicting, for example, the contamination level.

To this end, in many embodiments, the time-domain and frequency-domain signals are first captured by the terahertz imaging scanner and used to extract the various features, as described herein (FIG. 3). Next, some of the various features, for example peak field and delay, are used to find the sample boundaries, or safe zones, wherein a safe zone is defined as a smooth region on the sample which does not cause any abrupt change in the terahertz signal level. In many embodiments, these abrupt changes occur at the edge of the sample or due to a physical damage on the sample, and, therefore, only the measurements obtained for the safe zone, i.e., within the boundary of the sample, are used for irregularity evaluation by the algorithms of embodiments. Next, in many embodiments, the various features extracted from the data collected from the safe zones are used as an input for a machine learning data analysis model. In many embodiments, some samples prepared to have various thicknesses and contaminant/irregularity concentration levels are used to train the machine learning data analysis model first, in order to reliably obtain the absorption parameter as a function of the irregularity concentration. In many embodiments, once the machine learning data analysis model is trained, a new sample characterization is conducted as described in the flowchart of FIG. 3. More specifically, the various terahertz features of a new sample are extracted and used to determine the sample's boundary/safe zone. Next, the features extracted from the established safe zones are used to feed the trained neural network to predict irregularity contamination levels in these samples according to many embodiments.

In summary, in many embodiments, the data processing algorithms generally follow the steps described below.
(1) Selection of suitable measurements: to run the algorithm without any error, it is crucial to ensure the terahertz pulse transmits/reflects only through/from the sample/substrate; by monitoring the intensity and delay of the detected pulses relative to those from the reference signal, the algorithm selects a set of suitable measured signals.
(2) Evaluation of the suitable measurements:
 (a) Features of time-domain and frequency-domain signals are acquired.
 (b) An array of data is obtained by comparing (dividing and or subtracting) the features of the signal obtained from the sample points and those of the reference signal.
 (c) The array calculated from the features is used to train a machine learning model to predict an irregularity and or its concentration. The database to train the machine learning model is created by taking measurements on samples with a known irregularity measured by conventional detection techniques.
 (d) Different machine leaning models may be created for various substrates to be inspected and containing various types of irregularities in various concentrations by repeating the measurements described herein for many samples.
 (e) These machine learning models may be next used to determine the type of irregularity and its concentration for new measurements taken on different substrates/samples.

In some embodiments, the data processing algorithms of the instant disclosure are able to extract terahertz image data and quantitative information from multiple pixels of the focal plane array in parallel, boosting the scanning throughput. In some embodiments, the focal plane array has a small number of pixels, e.g. 15×15. In some embodiments, the focal plane array is 100×100 pixels large. In such embodiments, the terahertz imaging scanner is expected to offer a scanning time of less than 10 ms for scanning a 3×3 cm$^2$ area covered with, for example, agricultural produce samples. In some embodiments, a focal plane detector array is capable of taking three-dimensional terahertz snapshots of an area as large as ~10 cm$^2$ within less than a 100 ms, further increasing the scan speed and field-of-view of the terahertz imaging scanners of the embodiments. In some embodiments, a custom-tailored USB based evaluation board is utilized to read the pixel data from the focal plane array after its bonding to the evaluation board.

EXAMPLARY EMBODIMENTS

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

Detection of Hazardous Toxins in Produce

In many embodiments, the THz scanners and methods of the instant disclosure are used to identify and quantitate chemical contamination in a sample. In many such embodiments, the THz scanners and methods of the instant disclosure are used to detect and quantify hazardous toxins in agricultural produce or other foods. In many embodiments, the hazardous toxins are aflatoxins, which are highly hazardous mycotoxins that can contaminate agricultural products during both pre- and post-harvest stages (see, Bennett, J. W., et al., (2007), Aflatoxins: background, toxicology, and molecular biology. In Foodborne diseases (pp. 355-373), Humana Press, the disclosure of which is incorporated herein by reference). Although very high dosages of aflatoxins fluoresce under ultraviolet (UV) light (as described by Schmale, D. G., Munkvold, G. P., (2009), Mycotoxins in crops: A threat to human and domestic animal health, The plant health instructor, 3, 340-353; and Cassel, E. K., et al. (2001), Aflatoxins: Hazards in grain/aflatoxicosis and livestock, the disclosure of which are incorporated herein by reference), aflatoxins and the fungi that produce them may not be visible in contaminated food products to a naked eye, unlike other types of mold that can be easily spotted on food products. In general, the amount of biosynthesized aflatoxins varies depending on the strain of the fungus and the growth conditions. Furthermore, moisture, temperature, and insect damage are the most important environmental variables associated with aflatoxin contamination of agricultural commodities. However, complete prevention from aflatoxins is nearly impossible since they can even grow on crops under normal condition (Council for Agricultural Science, 2003, Mycotoxins: Risks in plant, animal, and human systems, No. 139, the disclosure of which is incorporated herein by reference). Therefore, high sensitivity detection of these toxins is crucial.

Figure 4:
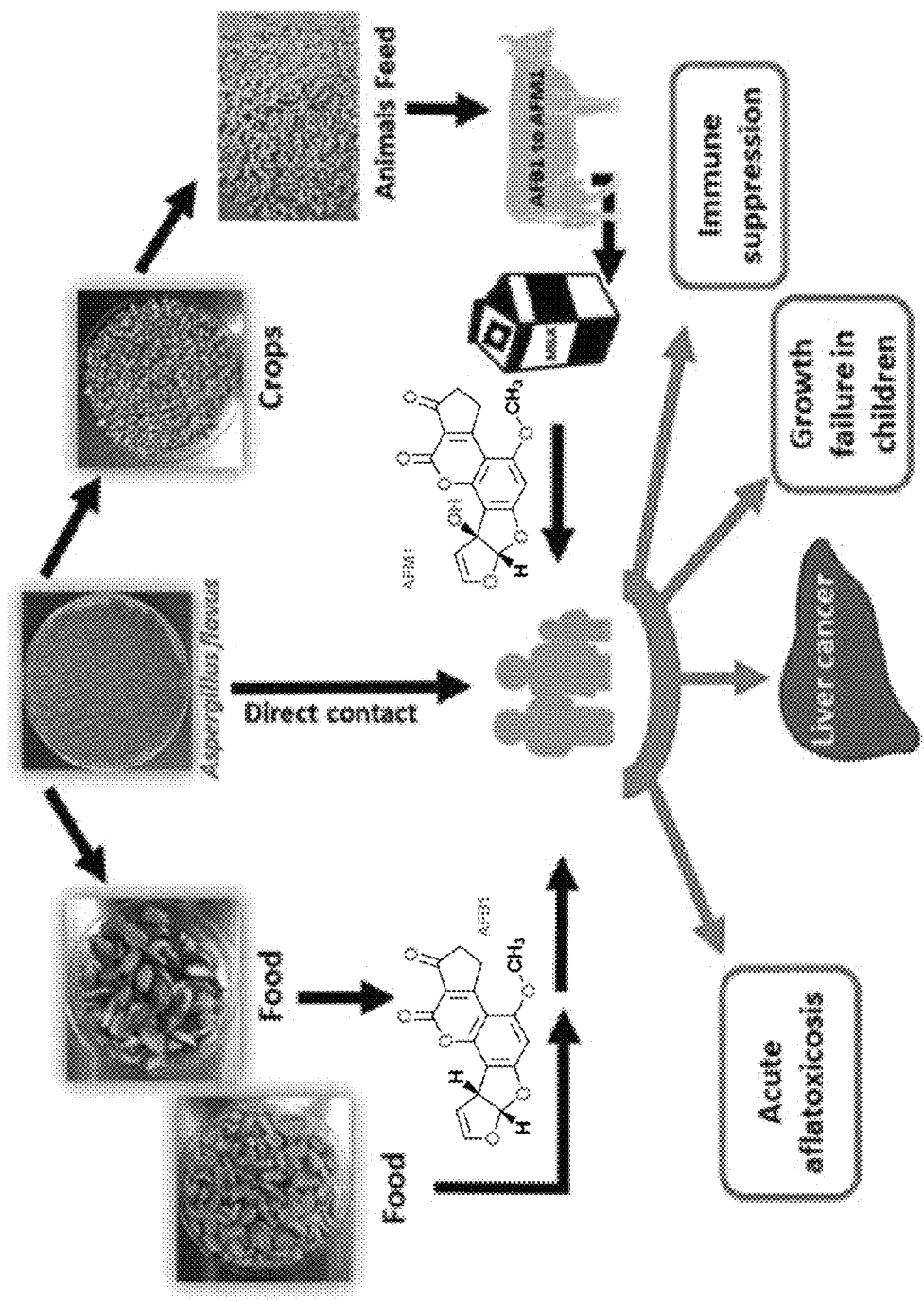
FIG. 4 provides a summary of the major aflatoxin contamination and exposure routes and their adverse health effects to humans, in accordance with prior art.

More specifically, mycotoxins, such as aflatoxins, are toxins produced by fungus found in agricultural products (FIG. 4, as seen in, for example: Alshannaq, A. F., et al., 2018, Controlling aflatoxin contamination and propagation of *Aspergillus flavus* by a soy-fermenting *Aspergillus oryzae* strain, Scientific reports, 8(1), 16871, the disclosure of which is incorporated herein by reference). Various types of aflatoxins exist. For example, Aflatoxin $B_1$ (AFB1 in FIG. 4), the most prevalent and the most toxic type of aflatoxin, is classified as Group I carcinogen by the International Agency for Research on Cancer (International Agency for Research on Cancer, 1979, IARC monographs on the evaluation of the carcinogenic risk of chemicals to humans, Some halogenated hydrocarbons. IARC monographs on the evaluation of the carcinogenic risk of chemicals to humans, the disclosure of which is incorporated herein by reference). High-dosage intake of AFB1 can result in acute effects and even sudden deaths, such as the 1966 outbreak in western India in which 100 people died due to aflatoxicoses (Krishnamachari, K. A. V. R., et al., 1975, Hepatitis due to aflatoxicosis: an outbreak in western India. The Lancet, 305(7915), 1061-1063, the disclosure of which is incorporated herein by reference). Aflatoxin $M_1$ (AFM1 in FIG. 4), a metabolite of aflatoxin $B_1$ in humans and animals, is also a chemical of concern, wherein the human exposure in nanogram levels may come from mother's milk. Other common poisonous aflatoxins include aflatoxins $B_2$, $G_1$, and $G_2$. Humans can intake aflatoxins either directly from plant foods, such as corn, peanuts, almonds, cotton, tree nuts, rice, figs, tobacco, and spices, or through animal products extracted from animals fed with crops containing aflatoxins (FIG. 4). The increasing dosage of aflatoxins in human body can cause various chronic health problems, including immunosuppression, growth retardation in children, and most importantly, liver cancer (Alshannaq, A. F., et al., (2018), Controlling aflatoxin contamination and propagation of *Aspergillus flavus* by a soy-fermenting *Aspergillus oryzae* strain, Scientific reports, 8(1), 16871, the disclosure of which is incorporated herein by reference). In fact, a strong correlation between liver cancer and aflatoxin exposure has been shown in various studies, and it is estimated that aflatoxins contribute to between 4.6 and 28.2% of liver cancer cases globally (Williams, J. H., et al., 2004, Human aflatoxicosis in developing countries: a review of toxicology, exposure, potential health consequences, and interventions, The American journal of clinical nutrition, 80(5), 1106-1122; Stevens, G., et al., 2009, WHO brochure», Bulletin of the World Health Organization, 87, 646-646, the disclosure of which are incorporated herein by reference). In the United States alone, 42,000 new cases of liver cancer (with survival rate of less than 25%) were predicted for 2019. However, both the prevention of aflatoxins contamination and its effective detection are extremely difficult.

Many chromatographic and immunochemical methods have been employed for the detection of aflatoxins (Wacoo, A. P., et al., 2014, Methods for detection of aflatoxins in agricultural food crops. Journal of Applied Chemistry, 2014, the disclosure of which is incorporated herein by reference). Among them, high-performance liquid chromatography coupled with mass spectroscopy (HPLC/MS) and enzyme-linked immunosorbent assay (ELISA) are the most-widely used techniques for aflatoxin detection (Kokkonen, M., et al., 2005, Determination of selected mycotoxins in mould cheeses with liquid chromatography coupled to tandem with mass spectrometry. Food additives and contaminants, 22(5), 449-456; Delmulle, B. S., et al., 2005; Development of an immunoassay-based lateral flow dipstick for the rapid detection of aflatoxin $B_1$ in pig feed, Journal of agricultural and food chemistry, 53(9), 3364-3368, the disclosure of which are incorporated herein by reference). Although these techniques can offer excellent sensitivity (detecting as little as 1 ppb amounts of aflatoxins), they are destructive (i.e., require grinding of the sample for the analysis), time consuming (require ~5 minutes per sample), and complicated (i.e., require highly trained personnel to perform). For these reasons, the currently employed aflatoxin detection techniques are only used for inspection of a small fraction of agricultural food products by regulatory inspectors before packaging and shipping to the distributors. In addition, spectroscopic methods, such as Fourier-transform infrared spectroscopy (FTIR) and fluorescence spectrophotometry, have also been used to detect aflatoxins (Pearson, T. C., et al., 2001, Detecting aflatoxin in single corn kernels by transmittance and reflectance spectroscopy, Transactions of the ASAE, 44(5), 1247; and Malone, B. R., et al., 2000, Determination of aflatoxins in grains and raw peanuts by a rapid procedure with fluorometric analysis. Journal of AOAC International, 83(1), 95-98, the disclosure of which are incorporated herein by reference), however, the sensitivity levels of these methods have not reached the threshold limit required by FDA for aflatoxins, which is 20 ppb for most products (Food and Drug Administration, USA (2000, August), Action levels for added poisonous or deleterious substances in food. Retrieved from https://www.fda.gov/Food/GuidanceRegulation/GuidanceDocumentsRegulatory-Information/ChemicalContaminantsMetalsNaturalToxinsPesticides/ucm077969.htm, the disclosure of which is incorporated herein by reference).

The use of terahertz waves is one promising approach to non-destructive and high-throughput evaluation of agricultural products for the presence of hazardous mycotoxins such as aflatoxins because of many advantageous characteristics of the THz radiation (Tonouchi, M., 2007, Cutting-edge terahertz technology. Nature photonics, 1(2), 97; Wang, C., et al., 2018, Terahertz Imaging Applications in Agriculture and Food Engineering: A Review; Qu, F., et al., 2018, Review of theoretical methods and research aspects for detecting leaf water content using terahertz spectroscopy and imaging, International Journal of Agricultural and Biological Engineering, 11(5), 27-34, the disclosure of which are incorporated herein by reference). However, no currently available THz-based technology can offer the sensitivity and resolution sufficient for practical large scale detection applications.

Nevertheless, many organic compounds have unique responses to the electromagnetic waves at terahertz frequencies. In fact, terahertz time-domain spectroscopy (THz-TDS) has been utilized to demonstrate that aflatoxins are spectrally-active at terahertz frequencies by making measurements on well-defined aflatoxin tablets. In addition, terahertz waves can penetrate through the most optically-opaque components of agricultural products and, therefore, provide chemical composition information about the plant regions deep under the sample surface. Furthermore, terahertz waves can penetrate through most packaging materials (plastic, paper, cardboard, foam, etc.), allowing their use for the evaluation of packaged food products. Moreover, terahertz waves do not pose any ionization hazard due to their low energy compared to high-frequency waves (UV, X-Rays). Together, these properties of terahertz wave-based spectroscopy make it an appealing platform for high-sensitivity, non-destructive detection of aflatoxins and other hazardous mycotoxins in agricultural food products.

However, despite the great potential of terahertz spectroscopy and even successful demonstration of an aflatoxin detection through terahertz scanning in a laboratory setting (Ge, H., et al., 2016, Quantitative determination of aflatoxin $B_1$ concentration in acetonitrile by chemometric methods using terahertz spectroscopy, Food chemistry, 209, 286-292; Chen, M., et al., 2014, A preliminary study of aflatoxin B1 detection in peanut oil by terahertz time-domain spectroscopy, Transactions of the ASABE, 57(6), 1793-1799, the disclosure of which are incorporated herein by reference), its use for high-sensitivity, high-throughput detection in a field setting is not practical with any of the currently available methods. Specifically, one of the main obstacles encountered in chemical detection with terahertz radiation methods is the low sensitivity of conventional terahertz scanners, which suffer from a trade-off between the signal-to-noise ratio (SNR) and measurement time. For example, to achieve a sufficiently sensitive measurement with conventional terahertz scanners, more than thousand measurements are usually taken to reduce the noise of the acquired data, which increases the measurement time significantly. In addition, most of the terahertz scanning measurements rely on meticulously and skillfully prepared samples, wherein the sample preparation recipes are not compatible with field settings (Pupeza, I., et al., 2007, Highly accurate optical material parameter determination with THz time-domain spectroscopy, Optics express, 15(7), 4335-4350; Ueno, Y., et al., 2006, Quantitative measurements of amino acids by terahertz time-domain transmission spectroscopy, Analytical chemistry, 78(15), 5424-5428, the disclosure of which are incorporated herein by reference).

Figure 5A:
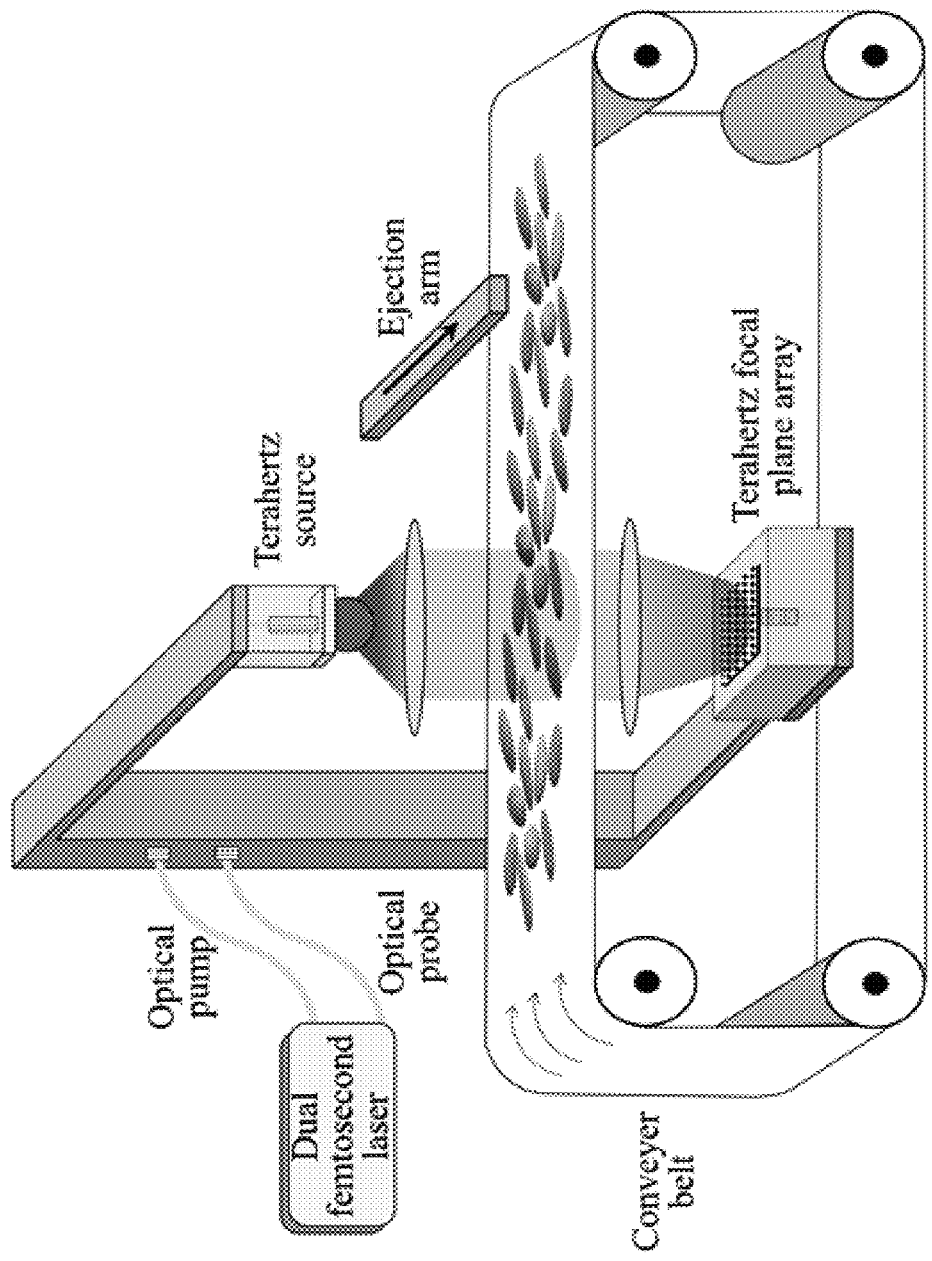
FIGS. 5A and 5B provide schematics of different designs for high-speed, contactless, non-invasive, and high-sensitivity terahertz imaging scanners for mycotoxins detection in agricultural produce, in accordance with embodiments of the invention.
Figure 5B:
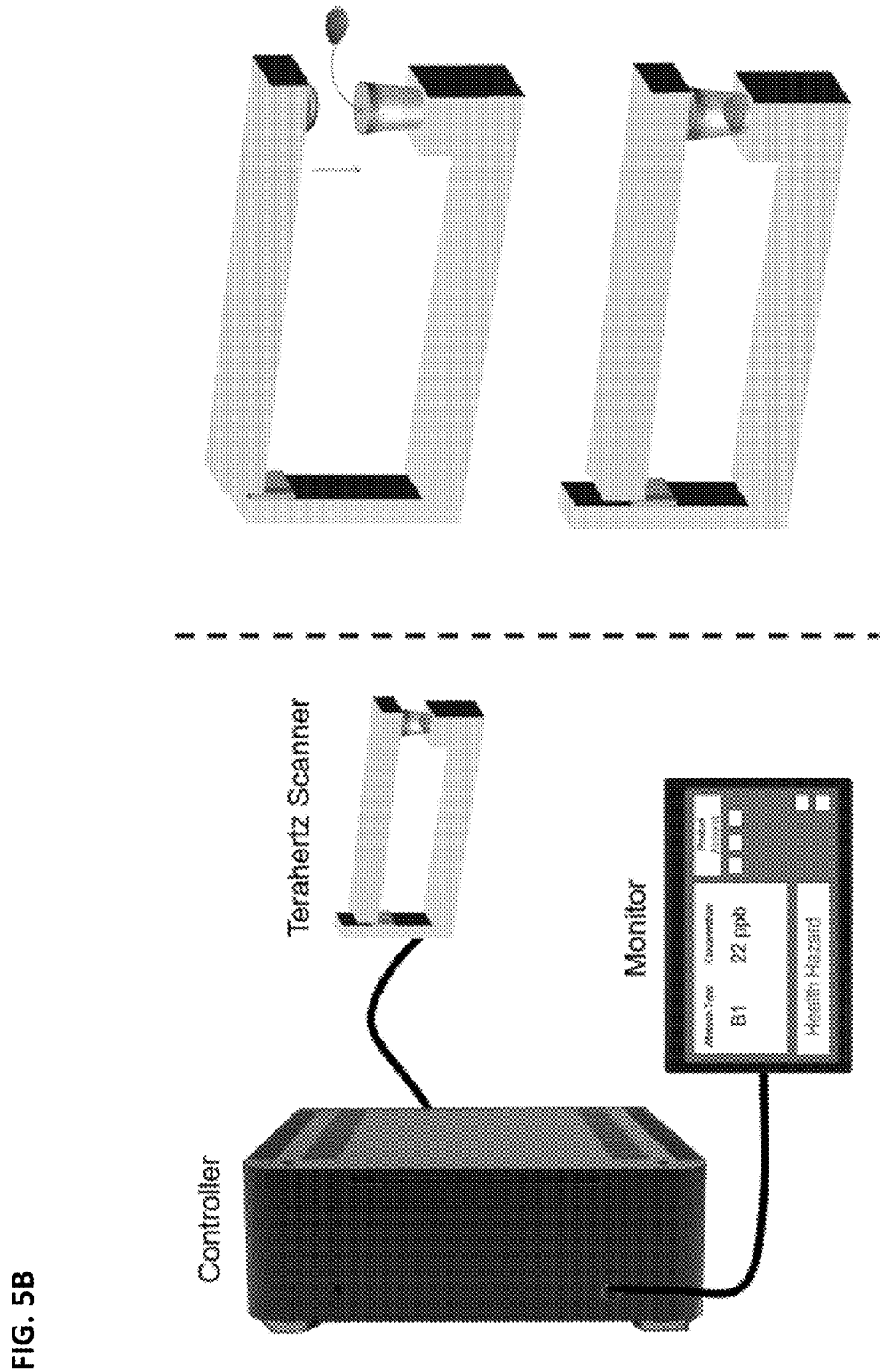

Nevertheless, in many embodiments of this application, a high-throughput, contactless, non-invasive, yet highly-sensitive detection of hazardous mycotoxins in agricultural produce is achieved with terahertz wave radiation methods and scanners described herein (FIGS. 5A and 5B). In many embodiments, the hazardous mycotoxins are aflatoxins. In many embodiments, the methods and scanners for the detection of hazardous mycotoxins address and overcome many limitations of the conventional terahertz scanning systems. For example, in many embodiments the methods and scanners of the application do not require special sample preparation or a skilled operator. In many embodiments, the methods and scanners of the application rely on a pulsed terahertz imaging system based on a plasmonic terahertz source and a focal plane array, which consists of a single plasmonic terahertz detector or a 2D array of plasmonic terahertz detectors. In many embodiments, the methods and scanners for the detection of mycotoxins rely on an advanced terahertz imaging algorithm described herein, wherein the algorithm is capable of direct calculation of mycotoxin concentration in the sample. In some embodiments, the algorithm relies on various terahertz parameters extracted from the data collected by measuring terahertz pulses transmitted and reflected from the examined samples. In some such embodiments, the algorithm relies on measurements of the intensity and delay of the terahertz pulses transmitted and reflected from the examined samples. In addition, in some embodiments, an enhanced plasmonic terahertz source and detector technology are used in the terahertz scanners of the instant disclosure for the mycotoxins' detection, and offer several orders of magnitude higher SNR levels compared to those offered by conventional terahertz sources and detectors. In many embodiments, especially wherein the hazardous mycotoxin is an aflatoxin, the detection sensitivity of the methods and scanners of the instant application is as low as 20 ppb or lower. In many embodiments, the detection sensitivity of algorithms, methods, and scanners of the instant application is as low as 5 ppb. In many such embodiments, the terahertz spectroscopy methods and scanners of the instant disclosure offer an excellent regulatory tool for high-throughput, non-destructive, contactless detection of mycotoxins and, in particular, aflatoxins in agricultural food products, minimizing regulatory non-compliance risks and providing high-quality products to the public. In many embodiments, the terahertz imaging scanner is handheld, as depicted in, for example, FIG. 5B.

In many embodiments, the detection of mycotoxins in agricultural food products and determination of the mycotoxin concentration level in the contaminated samples is accomplished with terahertz pulsed imaging. Among various techniques for non-invasive terahertz inspection, the terahertz pulsed imaging is the most powerful scheme, since it offers real-time hyperspectral amplitude and phase images over a broad terahertz frequency range. This unique combination of broadband amplitude and phase information enables extracting various important information about the examined agricultural products, such as their identity, composition, and concentration (Gowen, A. A., et al., 2012, Terahertz time domain spectroscopy and imaging: Emerging techniques for food process monitoring and quality control, Trends in Food Science & Technology, 25(1), 40-46; Baek, S. H., et al., 2014, Detection of melamine in foods using terahertz time-domain spectroscopy, Journal of agricultural and food chemistry, 62(24), 5403-5407; and Castro-Camus, E., et al., 2013, Leaf water dynamics of *Arabidopsis thaliana* monitored in-vivo using terahertz time-domain spectroscopy, Scientific reports, 3, 2910, the disclosure of which are incorporated herein by reference).

Figure 6A:
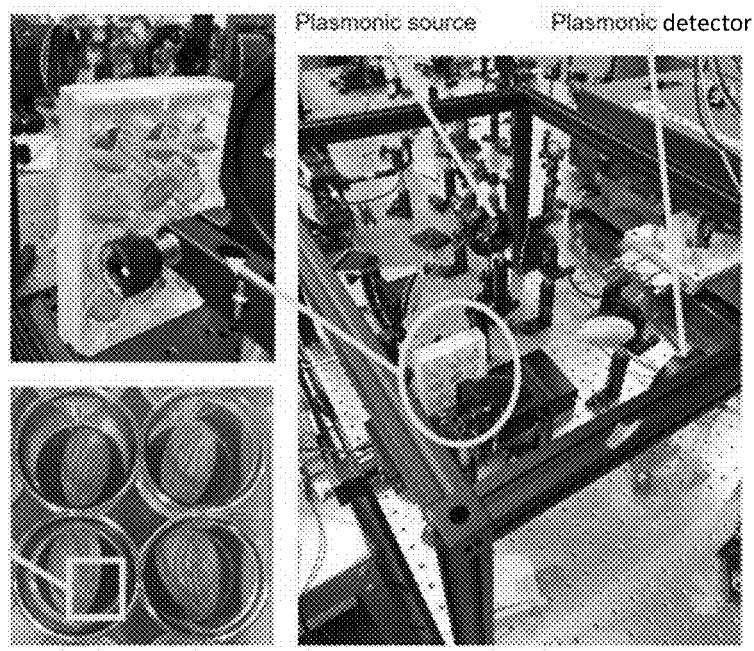
FIGS. 6A and 6B illustrate aflatoxins detection with an apparatus and methods of embodiments, wherein FIG. 6A provides an image of a benchtop terahertz pulse imaging scanner and an example of a detection setup.
Figure 6B:
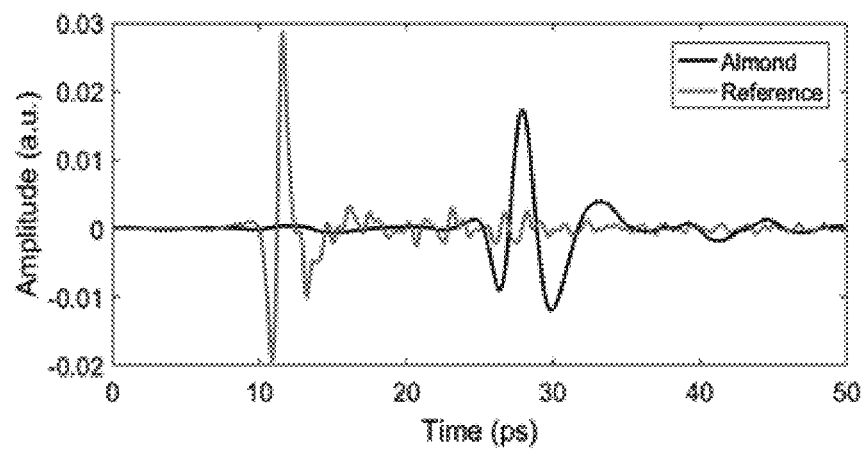

FIGS. 6A and 6B provide an illustrative example of aflatoxin detection in agricultural produce with the terahertz imaging scanner and methods of the instant disclosure according to many embodiments. For this example, aflatoxin-contaminated almond samples were prepared at Western Regional Research Center of Foodborne Toxin Detection and Prevention Department of USDA and probed with a benchtop version of the terahertz imaging scanner of embodiments. More specifically, individual solutions of most common poisonous aflatoxins, $B_1$, $B_2$, $G_1$, and $G_2$, were first prepared at concentrations of 500 ng/50 μl in benzene/acetonitrile (98/2) and used to spike individual almonds with aflatoxins in amounts of 20 ppb (the maximum allowed by FDA level of aflatoxin contamination in most agricultural food products), 100 ppb, and 400 ppb in triplicate. Next, three samples were measured for each combination of aflatoxin type and concentration. In addition, twelve untreated almond samples were also used as controls, to better examine aflatoxin interaction with terahertz radiation. Each almond was placed in a sealed well of a multi-well plate (FIG. 6A). A benchtop terahertz pulse imaging system/scanner (FIG. 6A) was set up with a high-power plasmonic terahertz source and a single-pixel plasmonic terahertz detector. The multi-well plates were mounted on a motorized two-axis translational stage and placed on the terahertz beam path in a way that the focused terahertz radiation transmitted through the plates. Multiple measurements on different locations of almond samples were taken by moving the two-axis translational stages.

Next, a data processing algorithm developed according to many embodiments of the instant disclosure may be employed to calculate the aflatoxins concentration (and, therefore, presence) from the raw data obtained by the terahertz imaging scanner of the embodiments. More specifically, data processing algorithms of embodiments calculate an absorption parameter, which represents mycotoxin concentration in a given sample. In many embodiments, the absorption parameter is independent from the samples' thickness and shape. To this end, FIG. 6B provides an example of raw data obtained by the terahertz imaging scanner of embodiments for an arbitrary point on one of the tested almonds from the set-up described in FIG. 6A, wherein the data comprises two terahertz pulse traces: a reference signal obtained when an almond sample does not intercept the terahertz beam (Reference), and a characteristic signal obtained when the focused terahertz beam propagates through an arbitrary point of an almond (i.e., sample) (Sample/Almond). It should be noted, that, according to many embodiments, the sample signal is required by the algorithms of embodiments to have all of the terahertz beam incident on the sample. Accordingly, it is desirable that the terahertz beam propagates through the central regions of the sample, however, it is not a necessary condition, as far as the entire terahertz beam propagates through the sample.

Figure 7A:
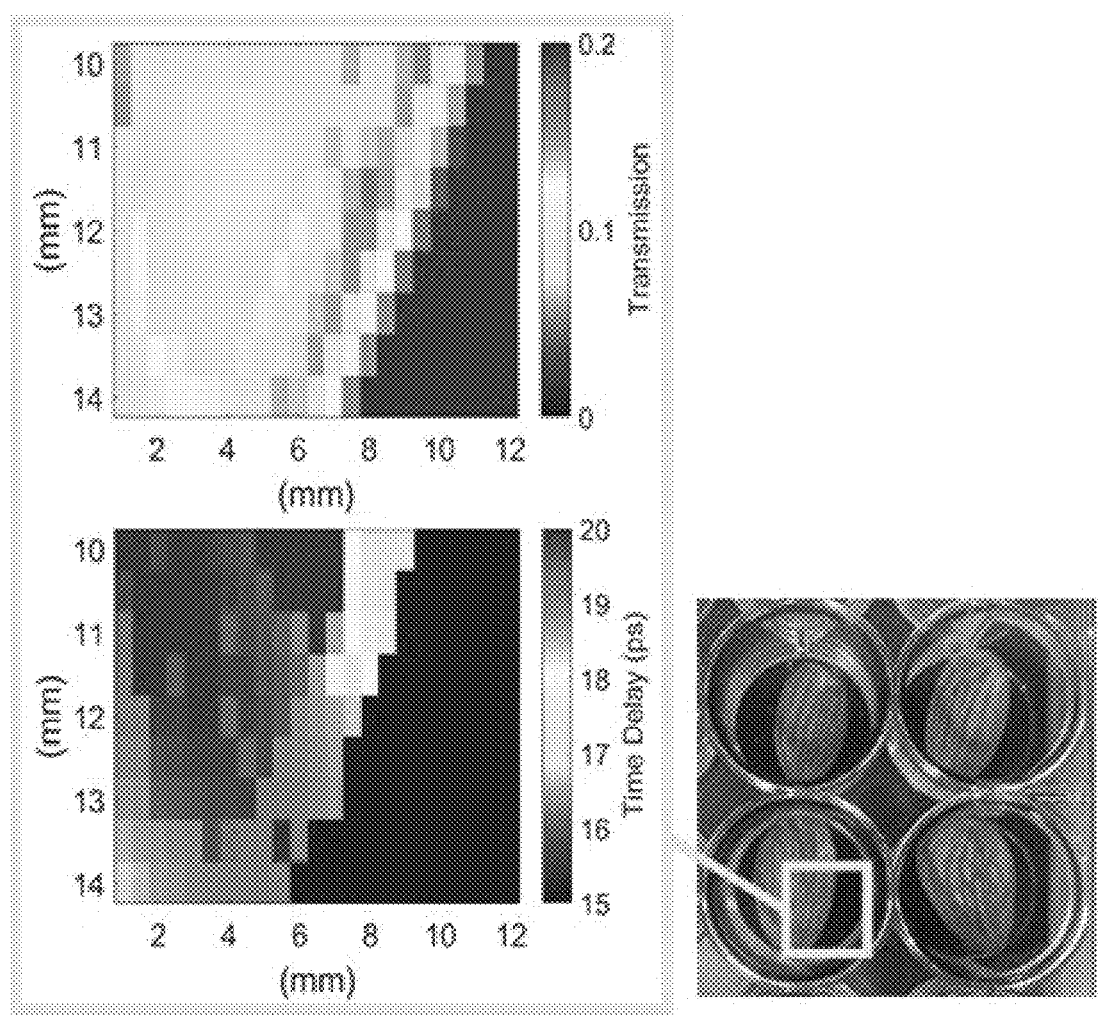
FIGS. 7A through 7D illustrate an example of a data processing algorithm of embodiments, wherein FIG. 7A provides examples of amplitude and delay images of a part of an almond sample obtained via such algorithm.
Figure 7B:
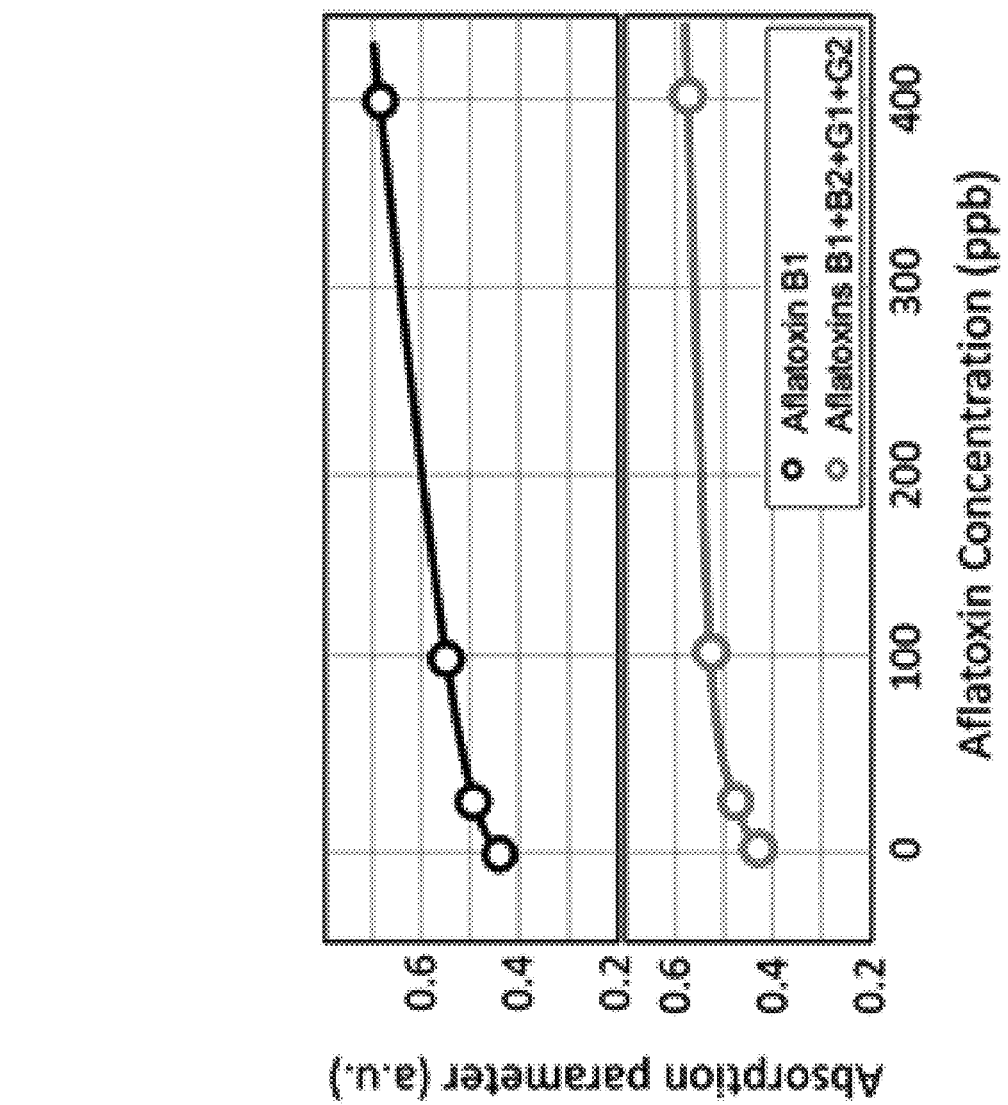

FIGS. 7A and 7B illustrate one data processing algorithm of embodiments, wherein the algorithm estimates the mycotoxin concentration by resolving an amplitude and a delay image of a scanned sample. More specifically, the amplitude image is obtained by calculating the ratio of the transmitted terahertz pulse over the reference pulse for each pixel (FIG. 7A, top). In addition, the delay image is obtained by calculating the delay of the transmitted terahertz pulse relative to the reference pulse (FIG. 7A, bottom). Next, this data processing algorithm of embodiments uses the amplitude and delay images, such as those depicted in FIG. 7A, to detect the edges of a sample and, then, to calculate an absorption parameter, which is the indication factor for aflatoxin concentration for the sample points. To this end, first, a safe zone is defined as a smooth region on the sample which does not cause any abrupt change in the terahertz signal level. These abrupt changes occur at the edge of the sample or due to a physical damage on the sample. Only the measurements obtained for the safe zone, i.e., within the boundary of the sample, are used for the absorption parameter calculation.

Furthermore, this data processing algorithm of embodiments uses the electromagnetic wave propagation formulas and Fresnel equations with complex refractive index to define the absorption parameter. Based on these formulas, the terahertz pulse transmission is proportional to $e^{-\alpha d}$, where $\alpha$ and d are the effective absorption and thickness of each sample point, respectively. Moreover, the terahertz pulse delay has a direct dependence on the effective thickness of each sample point. Therefore, in order to extract the effective absorption parameter, the data processing algorithm of embodiments runs an exponential curve fitting between the experimentally-measured amplitude and delay values for each sample point. FIG. 7B shows the outcome of such curve fitting, wherein the extracted absorption parameters of the healthy/untreated and aflatoxin contaminated samples plotted as a function of aflatoxins concentration. Accordingly, the aflatoxins detection results obtained for the setup shown in FIG. 6A demonstrate a clear increase in the absorption parameter as a function of the aflatoxin concentration for both aflatoxin $B_1$ (the most notorious and prevalent aflatoxin type present in 75% of aflatoxin-contaminated agricultural products) and other types of aflatoxins ($B_1$, $B_2$, $G_1$, and $G_2$). Therefore, the results of the experimental detection setup of FIGS. 6A and 6B used with, for example, the time-delay algorithm described in FIGS. 7A and 7B demonstrate that the terahertz imaging scanner and methods of many embodiments of the instant application offer adequate sensitivity to detect the maximum allowed by FDA aflatoxin contamination level (20 ppb).

Figure 7C:
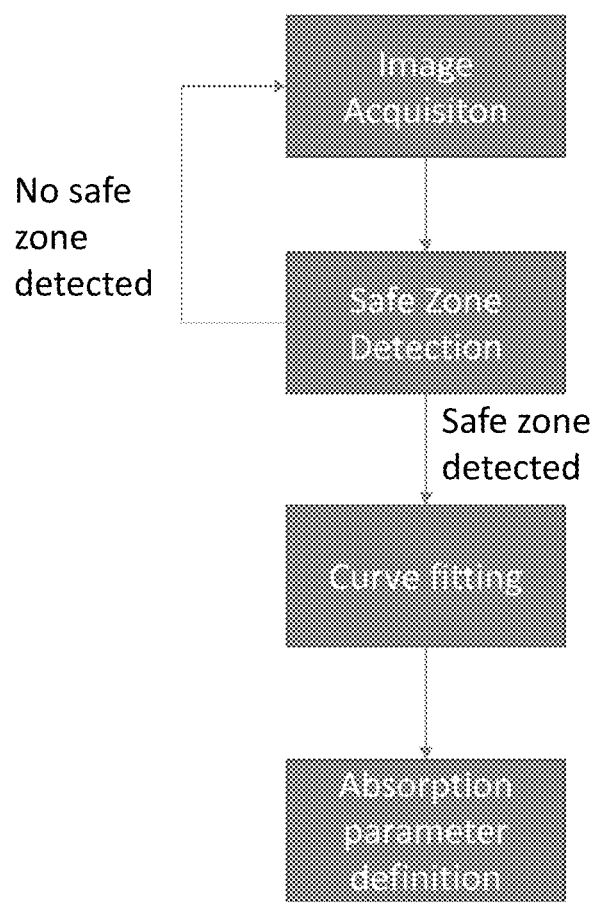
Figure 7D:
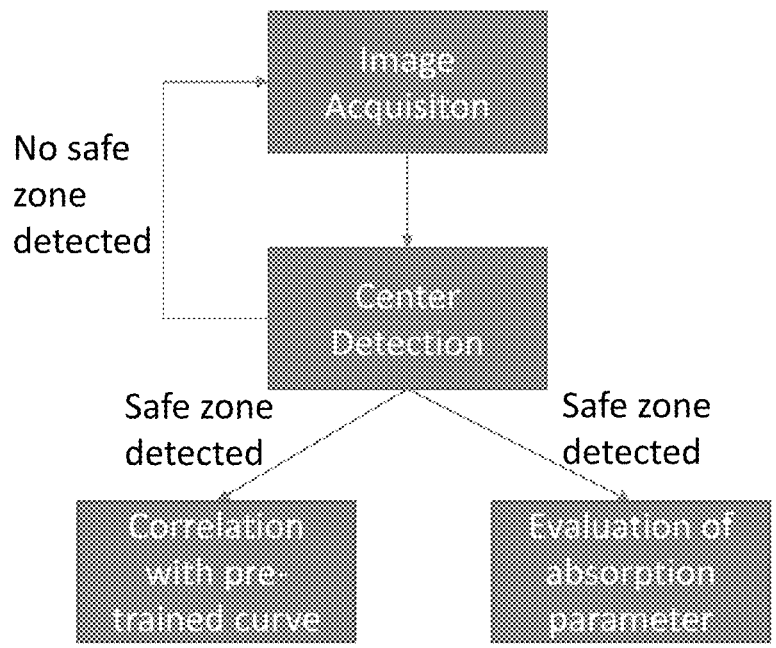

In addition, FIGS. 7C and 7D provide flowcharts that further explain the time-delay approach to the data processing algorithms of embodiments in more detail. Specifically, in order to successfully detect mycotoxins with this method, the data processing algorithm is first data trained as described in FIG. 7C. To this end, in many embodiments, multi-pixel images are first captured to create delay and amplitude images, as described above. Next, the delay and amplitude images are used to find sample boundaries, or safe zones, defined as a smooth regions on the sample which do not cause any abrupt change in the terahertz signal level. Next, the absorption parameter is calculated from terahertz wave measurements obtained for the safe zones. However, in order to reliably obtain the absorption parameter as a function of a mycotoxin concentration, many samples with various thicknesses and various mycotoxin concentration levels are first characterized with the terahertz imaging scanner of embodiments and curve fitted. In many embodiments, a curve relating the terahertz parameters (such as pulse delay-transmission) is calculated for each mycotoxin concentration level. In many embodiments, the absorption parameter is then defined from the formulas of these curves and the fit curves and absorption parameters are saved in a library.

Once the absorption parameter for a mycotoxin or mycotoxins of interest is established from the data training, wherein the absorption parameter is independent of the sample's thickness and shape, a new sample characterization is conducted as described in the flowchart of FIG. 7D. More specifically, the multi-pixel images are, yet again, captured to create delay and amplitude images according to embodiments, followed by sample boundary/safe zone determination. The safe zones are next used for absorption parameter calculation for the sample by using the fit curve formula according to embodiments. Next, the value obtained for the absorption parameter according to embodiments is compared to the values in the library to identify the mycotoxin concentration in a given sample.

In summary, in many embodiments, the time delay data processing algorithm of embodiments follows the steps described below.

(1) Selection of suitable measurements: to run the algorithm without any error, it is crucial to ensure the terahertz pulse transmits/reflects only through/from the sample; by monitoring the intensity and delay of the detected pulses relative to those from the reference signal, the algorithm selects a set of suitable measured signals.

(2) Evaluation of the suitable measurements.
   (a) A peak field ratio is defined and calculated by dividing the obtained signal's peak value by that of the reference signal.
   (b) A time delay is defined and calculated by subtracting the time indices of the peak values of the obtained signal and reference signal.
   (c) The peak field ratio has an exponential dependence on the calculated time delay and an absorption parameter, which indicates the mycotoxin concentration level. This absorption parameter is extracted by fitting the measured data to an exponential reference curve, which is produced for various samples of interest prior to the measurements. These exponential reference curves are produced by taking several measurements on samples with known mycotoxin concentration measured using conventional mycotoxin detection techniques.
   (e) A database of exponential reference curves is created for various food products (to be inspected) containing various types of mycotoxins and concentrations by repeating this measurement for many samples. This data database is used to determine the best fit for the mycotoxin type and concentration for new measurements taken on different agricultural food products.

Accordingly, in many embodiments, the time delay data processing algorithm of embodiments is data trained to identify the specific type of the detected mycotoxins in addition to the concentration of the contaminant. In many such embodiments, this data processing algorithm calculates the spectra of the transmitted terahertz pulses relative to the reference pulse by taking the Fourier transform of the time-domain traces, such as the traces shown in FIG. 6B, and correlating the extracted spectra with the terahertz spectral signatures of different types of mycotoxins.

Alternatively, the more general data processing and evaluation algorithm described in FIG. 3 may be employed with the terahertz imaging scanner of the instant disclosure in the mycotoxins' detection methods of embodiments. According to this approach, the data collected by the terahertz imaging scanner of embodiments is pre-processed to obtain time-domain and the corresponding frequency-domain signals for each sample point a measurement is taken. Furthermore, various features, such as peak field, delay, pulse width, spectral power, and phase, are extracted from the obtained time-domain and frequency-domain signals. Next, the data processing algorithm of embodiments uses the extracted various features to feed a machine learning data analysis model, such as, for example a dense neural network, which is, in turn, trained to predict the aflatoxin concentration for the sample points.

More specifically, in many embodiments, the data evaluation algorithm of embodiments uses a machine learning data analysis model trained to predict aflatoxin contamination in samples. In such embodiments, the machine learning data analysis model, such as, for example, a neural network, is fed by the various features extracted from the data comprising the time-domain and frequency-domain signals measured at each sample point by the terahertz imaging scanner of embodiments. According to many such embodiments, the extracted various features are directly related to the optical properties of the sample being analyzed for mycotoxin contamination, which is a function of aflatoxin type and contamination level. In many embodiments, some of the extracted various features are used to train the machine learning data analysis model, while others are used to evaluate the performance of the machine learning data analysis model by predicting the aflatoxin contamination level.

To this end, in many embodiments, the time-domain and frequency-domain signals are first captured by the terahertz imaging scanner and used to extract the various features, as described herein (FIG. 3). Next, some of the various features, such as, for example, peak field and delay, are used to find the sample boundaries, or safe zones, wherein, as explained above, a safe zone is defined as a smooth region on the sample which does not cause any abrupt change in the terahertz signal level. As also noted above, in many embodiments, these abrupt changes occur at the edge of the sample or due to a physical damage on the sample, and, therefore, only the measurements obtained for the safe zone, i.e., within the boundary of the sample, are used for aflatoxin contamination evaluation by the algorithms of embodiments. Next, in many embodiments, the various features extracted from the data collected from the safe zones are used as an input for a machine learning data analysis model of choice. In many embodiments, some samples prepared to have various thicknesses and mycotoxin concentration levels are used to train the machine learning data analysis model first, in order to reliably obtain the absorption parameter as a function of a mycotoxin concentration. In many embodiments, once machine learning data analysis model is trained, a new sample characterization is conducted as described in the flowchart of FIG. 3. More specifically, the various terahertz features of a new sample are extracted and used to determine the sample's boundary/safe zone. Next, the features extracted from the established safe zones are used to feed the trained machine learning data analysis model to predict aflatoxin contamination levels in these samples according to many embodiments.

In summary, in many embodiments, the data processing algorithms of embodiments generally follow the steps described below.

(1) Selection of suitable measurements: to run the algorithm without any error, it is crucial to ensure the terahertz pulse transmits/reflects only through/from the sample; by monitoring the intensity and delay of the detected pulses relative to those from the reference signal, the algorithm selects a set of suitable measured signals.

(2) Evaluation of the suitable measurements:
  (a) Features of time-domain and frequency-domain signals are acquired.
  (b) An array of data is obtained by dividing/subtracting the features of the signal obtained from the sample points by/from that of the reference signal.
  (c) The array calculated from the features is used to train a machine learning model to predict aflatoxin concentration. The database to train the machine learning model is created by taking measurements on samples with known mycotoxin concentration measured by conventional mycotoxin detection techniques.
  (d) Different machine learning models are created for various food products to be inspected and containing various types of mycotoxins and various toxin concentrations by repeating this measurement for many samples.
  (e) These machine learning models are used to determine the mycotoxin type and concentration for new measurements taken on different agricultural food products.

In many embodiments, the methods and scanners of the instant disclosure allow for maintaining large detection sensitivities and high scanning throughputs at the same time. In many embodiments, the terahertz imaging scanner and methods of the instant application offer adequate sensitivity to detect aflatoxin contamination levels below the minimum level of 20 ppb allowed by FDA. In many embodiments, the sensitivity level of the terahertz imaging scanner and methods is as low as 5 ppb. Furthermore, it should be noted, that although recent terahertz spectroscopy studies of aflatoxin $B_1$ tablets and liquid mixtures have already measured the terahertz spectral signatures of aflatoxin $B_1$, the terahertz imaging scanners of the instant disclosure offer several orders of magnitude higher SNR levels, as compared to the previously used systems, allowing to obtain terahertz spectral signatures of much higher accuracy. Accordingly, the terahertz imaging scanners and methods of the instant application may be used to fine tune and expand database libraries of the spectral signatures of different types of aflatoxins, other mycotoxins, or other toxins. In many embodiments, the thus enhanced libraries are used to improve the data processing algorithm of embodiments In many embodiments, the scanners and methods of the instant disclosure are suitable for the mycotoxin and, in particular, aflatoxin detection in agricultural produce that may include: corn, peanuts, cotton, tree nuts, rice, figs, tobacco, and spices. In such embodiments, the measurement methods, data processing algorithms, and post-processing techniques are calibrated and optimized for each food product to obtain the most accurate and sensitive results. In many embodiments, the scanners and methods of the instant disclosure are used to detect any desired toxin in a food sample, or any other type of a chemical contaminant in any food or inedible sample. In many embodiments, the terahertz imaging scanners and methods described herein allow for a real-time, fast, non-destructive quality control of agricultural food products or other samples of interest in any field, packaging, and or distribution settings. In many embodiments, the terahertz imaging scanners and accompanying systems are realized with a compact fiber-coupled packaging, and can be easily installed in any convenient settings.

Example 2

Detection of Defects in Lithium-Ion Battery Electrodes

In many embodiments, the THz scanners and methods of the instant disclosure are used to detect irregularities in a substrate. In many such embodiments, the high-performance terahertz scanners and methods of the instant disclosure provide a non-invasive, non-contact platform for various sensing and quality inspection applications. In some embodiments, the irregularities are defects or irregularities in a composite material. In some embodiments, the irregularities are defects in a battery electrode. In some such embodiments, the THz scanners and methods allow for in-line, real-time, non-contact, non-destructive evaluation (NDE) defect detection in lithium-ion battery (LIB) manufacturing, wherein the defect detection can be achieved during all roll-to-roll manufacturing process steps.

LIBs offer much higher capacity and energy density levels compared to conventional nickel-hydride batteries (see, for example, D. Howell, EV Everywhere Grand Challenge-Battery Obstacles and Opportunities, http://www1.eere.energy.gov/vehiclesandfuels/pdfs/ev_everywhere/5_howell_b.pdf, U.S. Department of Energy, 2012, the disclosure of which is incorporated herein by reference). Accordingly, this aspect has made this type of batteries the most desirable power generator for portable electronics and electric vehicles (EVs). However, the high cost of LIBs is still a big consideration and limits their applications. This cost could be significantly reduced with improved quality-control (QC) at very early stages of production cycle by identifying the flawed or sub-standard electrodes that are unknowingly assembled into the manufactured battery cells and, thus, decreasing the scrap rate (which is currently about 10% during production). Moreover, some of the problems associated with unknowingly incorporated defected electrodes include premature capacity fading, which results in lower lifetime of a battery, and thermal runaway, which can result in explosion. The QC is especially needed for LIBs, as they rely on flammable electrolytes, which can be source of a hazard. Accordingly, substantial efforts have been directed to developing non-destructive techniques for the characterization of defects in battery electrodes. For example, X-ray fluorescence (XRF) has been proven to be an effective tool for identifying electrode defects and evaluating variations in electrode coating thickness at a nanometer scale (Pietsch, P., & Wood, V. (2017). X-ray tomography for lithium ion battery research: A practical guide. *Annual Review of Materials Research*, 47, 451-479, the disclosure of which is incorporated herein by reference). However, the practical usage of such methods is limited by their very high costs and long measurement times. In addition, XRF utilizes ionizing radiation, which is a major safety hazard for manufacturing environments. As another approach, infrared (IR) thermography can also identify electrode defects (with fine special resolution around 20 μm), but it cannot offer depth information or evaluate the electrode coating thickness variations (Just, P., et al., (2016). A method to quantify coating thickness and porosity of electrodes for lithium-ion-batteries. *Measurement*, 89, 312-315; and Mohanty, D., et al., (2014). Non-destructive evaluation of slot-die-coated lithium secondary battery electrodes by in-line laser caliper and IR thermography methods. *Analytical Methods*, 6(3), 674-683, the disclosures of which is incorporated herein by reference). Alternatively, IR laser calipers can be used to evaluate electrode coating thickness variations, but they cannot detect flaws such as pinholes, divots, agglomerates, and blisters. Furthermore, optical imaging methods using CCD cameras cannot pick up certain types of electrode defects because the electrode coatings are generally black in color and, therefore, defects, such as scratches or reductions in thicknesses, cannot be detected optically. Yet another potentially useful methods for electrode defect detection is ultrasound time-of-flight imaging, however, it can only be implemented at very late stages of the manufacturing cycle, since it requires an ultrasound coupling medium (Hsieh, A. G., et al., (2015). Electrochemical-acoustic time of flight: in operando correlation of physical dynamics with battery charge and health. *Energy & environmental science*, 8(5), 1569-1577, the disclosure of which is incorporated herein by reference). However, most of pores, cracks, and non-uniform coatings are formed during the initial manufacturing steps and, therefore, early detection of these defects could greatly reduce the scrap rate of electrodes, scaling up the yield and throughput. Therefore, there exists a great need for a practical, real time, high throughput NDE systems and methods that can evaluate the structural integrity of lithium ion battery electrodes at early stages of manufacturing.

Accordingly, in many embodiments, the apparatuses and methods of the instant disclosure address the shortcomings of the existing LIB manufacturing inspection techniques by employing the terahertz time-domain spectroscopy (THz-TDS) for NDE applications. As such, the THz apparatuses and methods of embodiments, which use non-ionizing terahertz waves for scanning, do not pose any safety hazard to operators, nor are they destructive to the substrate/sample being analyzed. In addition, terahertz waves can penetrate through many non-metallic materials, including optically opaque materials, such as graphite and metal oxides used as electrode coatings. Consequently, THz waves can interact with substrates hidden below the surface of these materials, and they can be used to measure electrode coating thickness or detect defects beneath the surfaces, which cannot be visually observed. Moreover, the apparatuses and methods of embodiments can offer A-, B-, and C-scans in a single measurement, which allows for both spotting electrode defects and measuring electrode coating thickness. Furthermore, the THz scanners and methods of embodiments overcome many of the known limitations of the conventional terahertz radiation-based technologies, such as, for example, low sensitivity, which, in turn, leads to a trade-off between the SNR and measurement time, and, for the first time, enable effective in-line NDE applications.

In many embodiments, the detection of electrode defects with THz radiation, wherein the defect detection is high sensitivity and high throughput, is made possible by apparatuses and methods of the instant disclosure, which comprise use of THz scanners enhanced with plasmonic THz sources and detectors, combined with advanced image reconstruction and machine learning algorithms developed to accompany the THz measurements taken by the enhanced THz scanners. In many such embodiments, the use of the plasmonic terahertz source and detector technology significantly enhances terahertz radiation power and detection sensitivity levels of the THz systems that employ them, as compared to the conventional THz scanners, and, in turn, leads to improvements in the SNR levels by several orders of magnitude. As such, the improved SNR levels achieved for the THz scanners of embodiments enhanced with plasmonic source/detector technology allow to obtain higher accuracy data with a smaller number of measurements, thus shortening the data collection time and enabling real-time NDE. In addition, the use of advanced image reconstruction and machine learning algorithms of embodiments allow for direct identification of electrode defects and measurement of electrode coating thicknesses. More specifically, in contrast to the current data processing algorithms employed by conventional THz scanners, which use simple deconvolution techniques to measure coating thickness and use basic parameters obtained from THz-TDS measurements to create images, the algorithms of embodiments utilize deep learning techniques that enable identification of very small variations between defect-free and defective parts with a sub-wavelength resolution.

Figure 8:
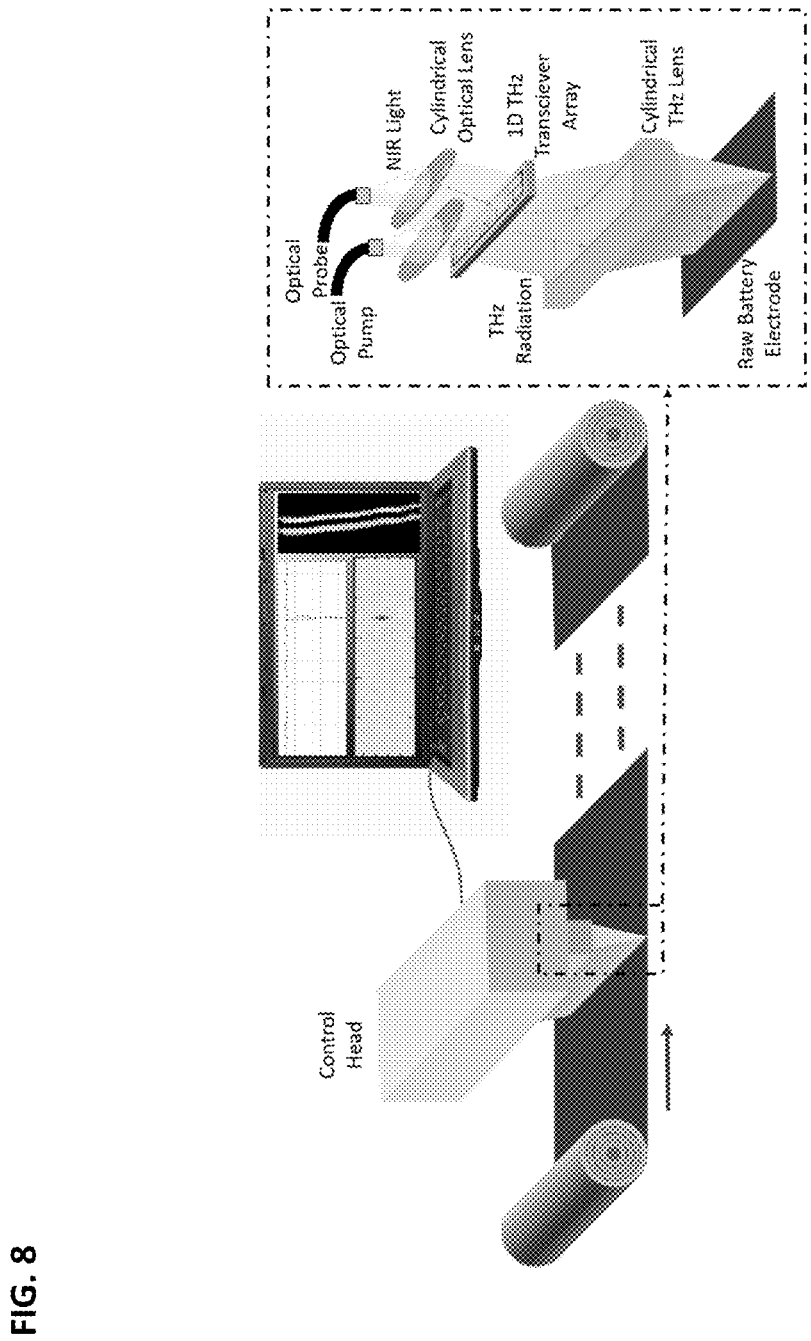
FIG. 8 schematically illustrates the terahertz scanner for real-time, non-contact, non-invasive, and high-accuracy identification of defects in LIB electrodes during a roll-to-roll manufacturing process in accordance with embodiments of the invention.

To this end, in many embodiments, an in-line terahertz scanner is used with advanced algorithms of the instant application for real-time, non-contact, non-invasive, and high-resolution identification of defects in LIB electrodes during the roll-to-roll LIB manufacturing process, as, for example, schematically depicted in FIG. 8. In such embodiments, the THz scanner at least comprises a THz source and a THz detector operating in the terahertz frequency band of the electromagnetic spectrum. In many embodiments, the THz scanner comprises a one-dimensional (1D) array of plasmonics-enhanced photoconductive terahertz transceivers controlled by a near-infrared (NIR) pump-probe light. In many embodiments, the total length of the transceiver array matches the width of the moving LIB electrodes. In many embodiments, each transceiver element consists of a terahertz source-detector-pair fabricated side-by-side. In many embodiments, a combination of cylindrical optical lenses is used to provide a line focus for the NIR pump and probe beams on the 1D array of the THz sources and the THz detectors, respectively. In many embodiments, as the THz source is pumped by the NIR beam, an elliptical shaped terahertz radiation is generated. In many such embodiments, the generated THz radiation is then focused onto a line covering the entire width of the LIB electrode using a cylindrical terahertz lens. According to many embodiments, the THz radiation reflected from the battery electrode being scanned is re-focused on the 1D array of the terahertz detector probed by the NIR beam. In many embodiments, the THz source and THz detector comprise plasmonic nano-antenna arrays that offer enhanced radiation power levels and detection sensitivities, as well as large field-of-views that are all critical for high-accuracy, high-throughput operation of THz scanners of the instant application.

Accordingly, in many embodiments the defect detection methods of the instant application are based on the interaction of broadband terahertz pulses with the substrate/sample under test. In many such embodiments, the THz scanner of embodiments collects the pulses reflected from the tested substrate, such as, for example, a LIB electrode. Since terahertz pulses can penetrate through a plurality of layers that may coat the substrate (wherein the substrate is, for example, an electrode), and since a fraction of their power reflects from each layer interface, a time-of-flight terahertz image can be obtained to identify structural problems beneath the surface of the substrate's coating, if any, according to many embodiments (Anastasi, R. F., & Madaras, E. I. (2006, March). Terahertz NDE for under paint corrosion detection and evaluation. In *AIP Conference Proceedings* (Vol. 820, No. 1, pp. 515-522). American Institute of Physics; and Anastasi, R. F., & Madaras, E. I. (2006, March). Terahertz NDE for metallic surface roughness evaluation. In *Nondestructive Evaluation and Health Monitoring of Aerospace Materials, Composites, and Civil Infrastructure V* (Vol. 6176, p. 61760O). International Society for Optics and Photonics, the disclosures of which is incorporated herein by reference). In addition, in many embodiments, the time delay between reflected pulses from different interfaces allows for measurement of the thickness of any such coatings. In fact, various THz-TDS setups are commercially available to measure coating thicknesses in auto industry (Krimi, S., et al., (2016). Highly accurate thickness measurement of multi-layered automotive paints using terahertz technology. *Applied Physics Letters*, 109(2), 021105, the disclosure of which is incorporated herein by reference). In many embodiments, due to the contactless nature of the THz methods of the instant application, they can be used to measure both wet and dry coatings.

In many embodiments, the data captured by the THz scanners of the instant disclosure from the line scans of the LIB electrodes is processed in real-time to identify defects. In many embodiments, the THz scanners and algorithms are capable of recognizing any kind of defects from small pores or cracks to coating thickness variations. In many embodiments, the field-of-view of the THz scanner is adjusted to cover the entire width of the electrode (for example, 21.5 cm). In some embodiments, the THz scanner of the instant application offers more than a 50 dB SNR over the 0.1-3.5 THz frequency range for a line scan measurement time of 5 milliseconds, while using a 1D array of terahertz sources and detectors with a 1 mm×1 mm area each. Accordingly, in many embodiments, the THz scanner can capture images of the rolling battery electrodes with an image pixel pitch less than 1 mm×1 mm, even at the fast roll-to-roll manufacturing speed of 10 meters/min, which produces less than a 1 mm displacement of a substrate during 5 milliseconds. In some embodiments, the THz scanner is a bench-top scanner unit comprising a single pair of a 1 mm×1 mm THz source and a 1 mm×1 mm THz detector.

Figure 9:
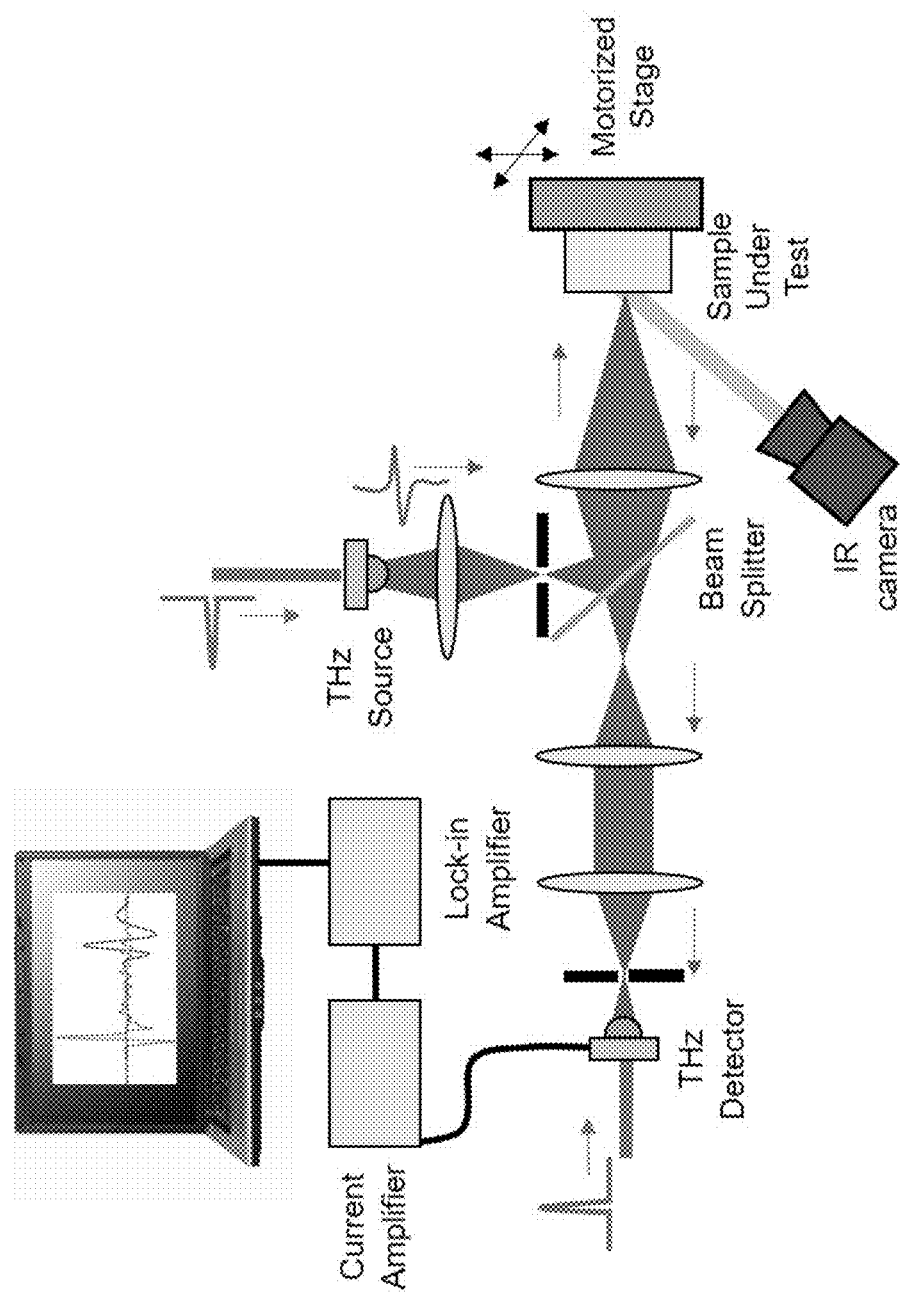
FIG. 9 schematically illustrates a THz-TDS setup in reflection mode modified with a confocal microscopy scheme and an integrated IR camera in accordance with embodiments of the invention.

In some embodiments, the THz scanner is a THz-TDS scanner enhanced with a confocal microscopy scheme and an integrated IR camera, as schematically depicted in FIG. 9. In many such embodiments, the THz scanner is adjusted to focus the reflected terahertz radiation from different spots of the samples to the terahertz detector. In many such embodiments, the samples may be placed on a motorized stage, wherein the terahertz images are acquired through raster scanning. In some embodiments, wherein a confocal microscopy scheme is adopted as shown in FIG. 9, a high image contrast is achieved and the system's resolution is pushed to the diffraction limit by placing two pinholes: one after the source (to clean the terahertz beam from aberrations) and the other before the detector (to get rid of the unwanted scattered beam components). In many embodiments, an IR camera is also integrated with the THz scanner setup to simultaneously take high resolution IR images of the studied samples. As such, the resolved terahertz images of embodiments may be mapped to the high-resolution IR images, allowing to label which pixels on the terahertz images correspond to defective parts to increase the accuracy of the data analysis and machine learning algorithms as needed.

In many embodiments, the THz scanners are used with advanced data analysis algorithms. With conventional approaches, terahertz imaging systems cannot offer high resolution due to the diffraction limit of the terahertz radiation, wherein 1 THz corresponds to 300 μm wavelength. Accordingly, in some instances, the terahertz wavelengths could greatly exceed the size of defects in a battery electrode. In other words, although it is possible to achieve high depth resolutions with well-established deconvolution techniques, lateral resolution of conventional terahertz imaging systems cannot be pushed beyond the diffraction limit. However, the image processing and machine learning algorithms of many embodiments allow identification of many such small defects, including defects with feature sizes much smaller than the diffraction limit. More specifically, in many embodiments, the advanced data analysis algorithms consider a defective electrode region to behave as a collection of independent scatterers, wherein the amount of the scattered radiation is proportional to the scatterer cross-section (i.e., defect size). In such embodiments, even a very small and shallow defect causes at least a small change in the scattered/reflected terahertz signal. As such, the advanced data analysis algorithms of the instant application, which comprise image processing and machine learning modalities, enable identification of extremely small (especially as compared to the terahertz wavelengths) differences between defect-free and defective regions of the electrodes under inspection for NDE applications. In many embodiments, the THz scanners used with the algorithms and methods of the instant disclosure (i.e., the overall THz system and methods framework), which improve the sensitivity of the THz scanners, can identify defects with a feature size of only a few micrometers (<10 micrometers).

Figure 10A:
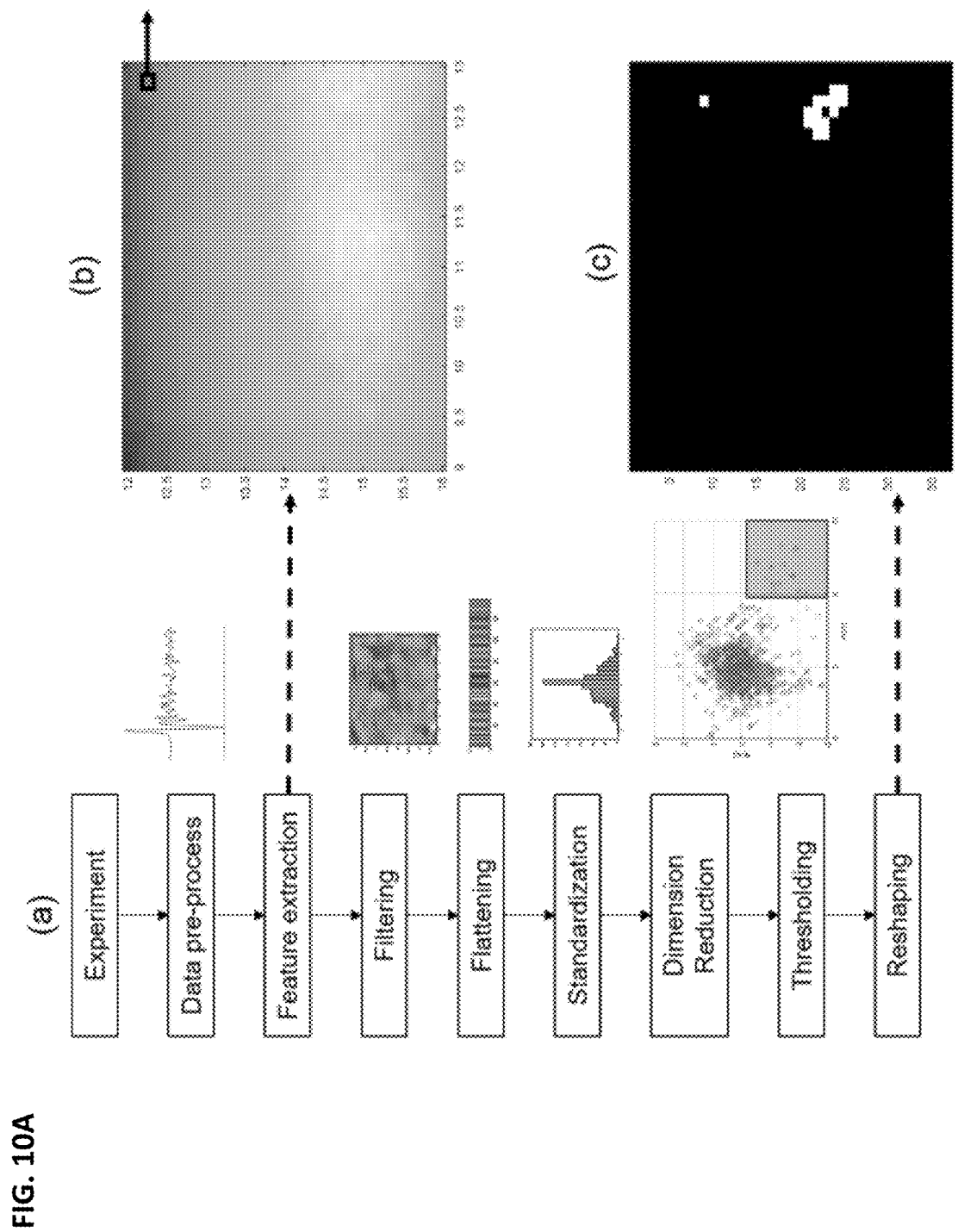
FIG. 10 provides a flowchart describing two advanced data processing and evaluation algorithms that may be employed in the detection of LIB electrode defects in accordance with embodiments of the invention, wherein flowchart portions (a) shows the flowchart of the image processing and the unsupervised learning modality, flowchart portion (b) provides an example of raw terahertz amplitude image, flowchart portion (c) provides an example of processed terahertz image, flowchart portion (d) shows an exemplary spectrogram of a single pixel from the raw terahertz amplitude image in (b), and flowchart portion (e) illustrates a convolutional network diagram.
Figure 10B:
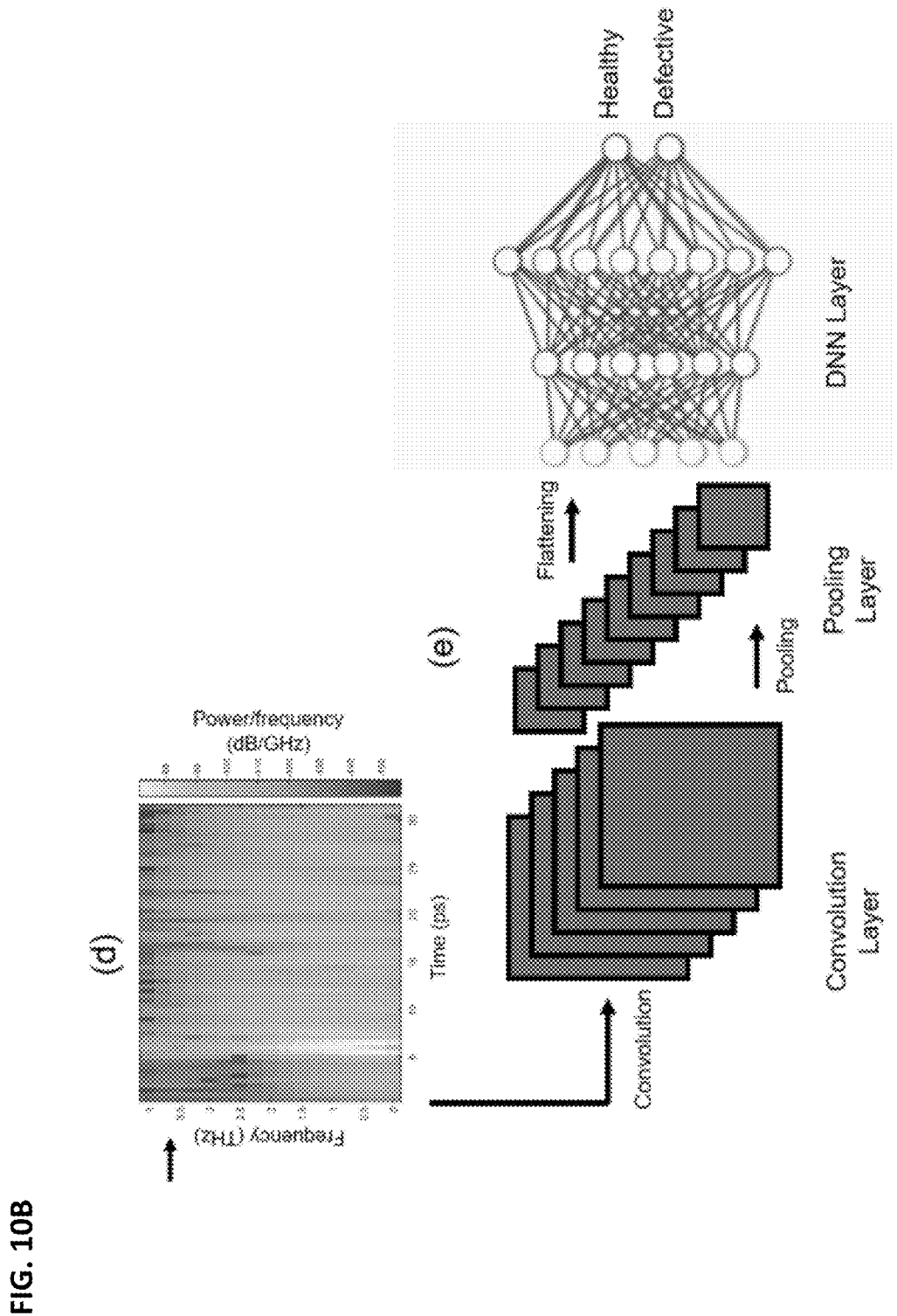
Figure 11A:
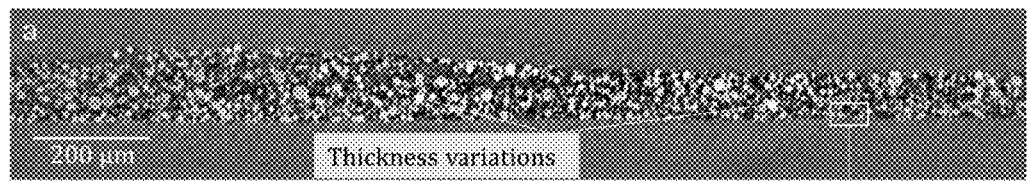
Figure 11B:
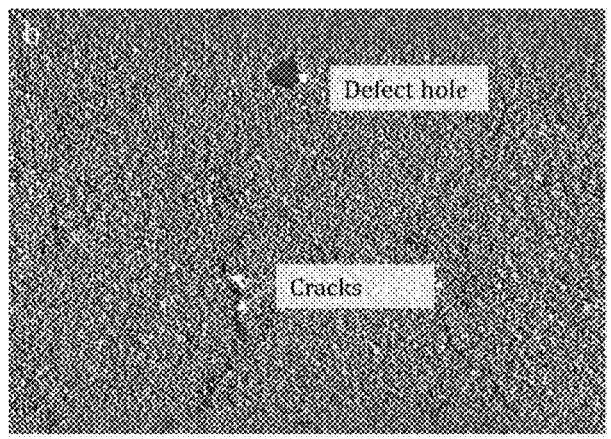
Figure 11C:
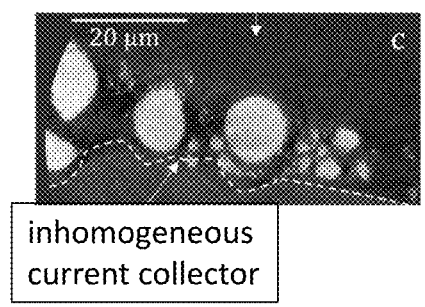
Figure 11D:

The advanced data analysis algorithms of the instant application comprise at least two efficient frameworks that may be used in the detection of sub-wavelength substrate defects in various quality control applications according to many embodiments. In many such embodiments, the first of the at least two frameworks is based on an unsupervised machine learning modality as outlined in FIG. 10. According to the first, unsupervised, framework, various features are first extracted from the time- and corresponding frequency-domain signals captured by the THz scanner of the instant application. Next, in many embodiments, after applying high-pass and median filters, the extracted images are flattened, standardized, and used as an input for an autoencoder. In many embodiments, the design of the autoencoder can be modified according to the specific application type and data size. In many embodiments, the encoding part of the autoencoder is trained to reduce the multi-dimensional feature map to only two dimensions (Ng, A. (2011). Sparse autoencoder. *CS294A Lecture notes*, 72(2011), 1-19, the disclosure of which is incorporated herein by reference), followed by choosing a threshold according to the standard deviation of the outputs. For example, image (b) in FIG. 10 shows a raw terahertz image obtained by using the captured peak time-domain signal at each sample point, according to many embodiments. Here, although it was verified that the sample contains a ~20 μm-diameter hole created with a pinhole, the raw terahertz image (b) does not show this defect, but only shows a gradual variation in the reflected terahertz signal due to the use of a slightly warped sample. However, processing the signal with the advanced data algorithm using the autoencoder of embodiments yields an image, such as shown in image (c) of FIG. 10, which clearly identifies the defect in question.

In many embodiments, the second of the at least two advanced data analysis algorithm frameworks utilizes supervised machine learning, as also outlined in FIG. 10. In many such embodiments, each pixel on an image obtained from the THz scanner of the application corresponds to a time-domain signal and a corresponding frequency-domain signal. Accordingly, in many embodiments, a spectrogram for each pixel is created for time-frequency analysis, as shown in images (b) and (d) of FIG. 10, provided here as an example. In many such embodiments, in turn, the spectrogram obtained for each pixel is used to feed a machine learning data analysis model, such as, for example, a convolutional neural network that consists of several convolution and pooling layers as well as a densely connected neural network, as depicted in scheme (e) of FIG. 10 (LeCun, Y., & Bengio, Y. (1995). Convolutional networks for images, speech, and time series. *The handbook of brain theory and neural networks*, 3361(10), 1995, the disclosure of which is incorporated herein by reference). In many such embodiments, next, a part of the measurement results is used for training the machine learning data analysis model, while the other part is used for validation of the algorithm. In some embodiments, in this supervised machine learning framework, the pixels corresponding to the defective parts of the sample may be also labeled through using an IR camera system integrated with the THz scanner of embodiments as illustrated, for example, in FIG. 9. In many embodiments, the supervised machine learning framework described herein offers a nearly 99% accuracy in detecting sub-wavelength substrate defects. In many embodiments, both the supervised and the unsupervised machine learning frameworks of the advanced data analysis algorithms of the instant application may be optimized for any desired quality control application. In many embodiments, the advanced data analysis algorithms of the instant application are optimized for LIB inspection applications.

Table 1 below provides a comparison summary for several QC methods currently used as NDE techniques for defect detection in LIB and compares such methods to the THz methods of embodiments. In addition, FIGS. 11A-11D provide examples of various battery electrode defects amenable to detection by real time, high throughput, yet high sensitivity THz methods of the instant disclosure. In many embodiments, the defects suitable for detection analysis by the THz systems and methods of embodiments include, but are not limited to, all of the defects selected from the list comprising: cracks and holes of sizes between 10 μm and 1 mm, current collector bends, thickness variations, and any combination thereof. For example, FIGS. 11A-11D show examples of defects present in a commercial NCM cathode, wherein macroscopic crack and hole defects, as well as microscopic (~10 μm in size) bends in the current collector are visualized by X-ray CT, but could be more efficiently and safely detected by the THz methods according to many embodiments. Moreover, the defects in the current collector are currently not possible to observe with optical or XRF techniques, yet the THz scanner and methods of embodiments are perfectly fit for resolving these types of heterogeneities.

TABLE 1

Specifications of the proposed terahertz scanner and their comparison with other NDE techniques used for defect detection in LIB electrodes and coatings.

| | Health Hazard | Non-Contact Scanning | Real-Time QC on R2R manufacturing | Pre-Packaging Defect Detection | Defect Detection | Coating Thickness Measurement | Depth Resolution | Lateral Resolution |
|---|---|---|---|---|---|---|---|---|
| XRF | Yes | Yes | No | Yes | Yes | Yes | <1 μm | <1 μm |
| IR Thermography | No | Yes | Yes | Yes | Yes | No | NA | 20 μm |
| Laser caliper | No | Yes | Yes | Yes | No | Yes | 20 μm | NA |
| Ultrasound Imaging | No | No | No | No | Yes | Yes | 100 μm | 100 μm |
| Electrical Testing | No | No | No | No | Yes | No | NA | NA |
| THz Imaging | No | Yes | Yes | Yes | Yes | Yes | 10 μm | 10 μm |

Figure 12D:
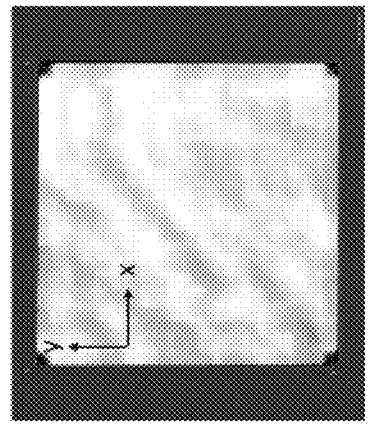
Figure 12E:
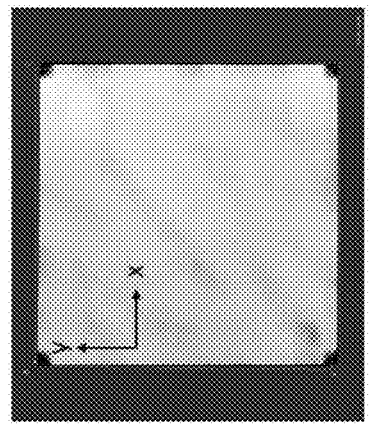
Figure 12A:
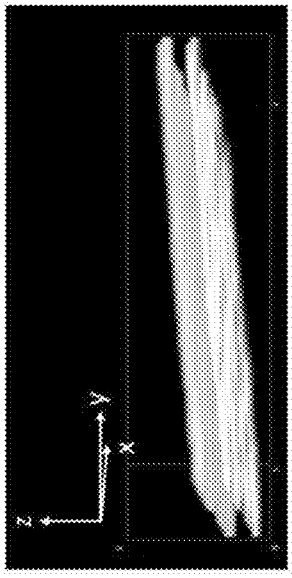
Figure 12B:
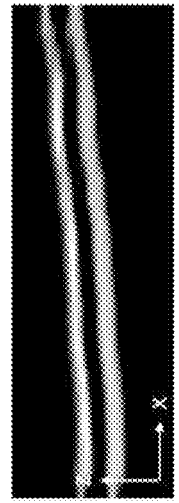
Figure 12C:
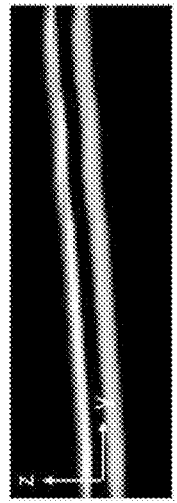

In addition, FIGS. 12A-12E illustrate substrate imaging capabilities of a conventional THz system and methods, showing that even a THz method without the hardware and software enhancements of embodiments is still a powerful tool for electrode imaging. More specifically, FIG. 12A shows an exemplary 3D terahertz image obtained from an anode electrode comprising a composite graphite with binder and additive conducting material coated onto a Cu foil (10 μm thick) with a thickness range of 50-200 μm (which is an industrially relevant range) through a conventional THz-TDS setup in reflection mode. To obtain this image, a prior art deconvolution technique, Two-step Iterative Shrinkage/Thresholding (TwIST) Algorithm, which offers ~10 μm depth resolution, was applied to the time-domain terahertz signal acquired at each sample point (Utkin, V. I., & Poznyak, A. S. (2013). Adaptive sliding mode control with application to super-twist algorithm: Equivalent control method. *Automatica*, 49(1), 39-47; Bioucas-Dias, J. M., & Figueiredo, M. A. (2007, September). Two-step algorithms for linear inverse problems with non-quadratic regularization. In 2007 *IEEE International Conference on Image Processing* (Vol. 1, pp. I-105). IEEE; and Chen, Y., et al., (2011). Total variation deconvolution for terahertz pulsed imaging. *Inverse Problems in Science and Engineering*, 19(2), 223-232, the disclosures of which is incorporated herein by reference). The captured 3D image was further processed to observe cross-sectional images of the electrode sample provided in FIGS. 12B and 12C. The image of each layer can also be obtained by windowing the deconvolved time-domain signal, such as the imaged provided in FIGS. 12D and 12E.

In many embodiments, the effective, high-throughput detection of defective parts in LIBs throughout the whole manufacturing process, including practical roll-to-roll manufacturing processes, by the THz systems and methods of the instant application significantly reduces the scrap rate of LIB manufacturing, and, therefore, improves LIBs' costs and environmental impact, as well as safety of LIBs. In addition, in many embodiments, the THz systems and methods of the instant application create a feedback loop for investigating the correlation of defect characteristics with cell performance and capacity. In many such embodiments, pass/fail criteria for electrodes may be developed, wherein such criteria are defined via a function of type, size, and density of the defects.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method for identifying chemical and structural irregularities in a substrate, comprising:
    providing a sample comprising a plurality of points and having chemical or structural variations;
    providing a terahertz scanner comprising:
        at least one terahertz source generating a terahertz beam along a terahertz beam path, and
        at least one terahertz detector, wherein
        the terahertz scanner produces a characteristic signal when the terahertz beam is detected by the at least one terahertz detector after interacting with a point of the plurality of points of the sample; and
        the terahertz scanner produces a reference signal when the terahertz beam is not intercepted by the sample;
    obtaining a characteristic signal and a reference signals for at least one point of the plurality of points of the sample;
    extracting one or more characteristic features from a characteristic data set afforded by the characteristic signal, and extracting one or more corresponding reference features from a reference data set afforded by the reference signal; wherein at least one of the characteristic features and the corresponding reference features are selected from a list consisting of: peak intensity, average intensity, delay, pulse width, spectral power, phase of the characteristic signals, and any combination thereof;
    analyzing the characteristic features and the corresponding reference features using a machine learning data analysis model to find chemical and or structural information about the sample; and
    recognizing irregularities in or differences between the characteristic features and the corresponding reference features to identify the chemical or structural variations in the sample.

2. The method of claim 1, wherein the machine learning data analysis model is selected from a list consisting of: supervised model, unsupervised model, and any combination thereof.

3. The method of claim 1, wherein the machine learning data analysis model is trained to recognize the chemical or structural variations in the sample.

4. The method of claim 1, wherein the terahertz scanner is a terahertz time-domain spectroscopy scanner.

5. The method of claim 4 wherein the terahertz scanner further comprises:
a femtosecond laser generating an optical beam, and
a plurality of optical lenses for focusing the optical beam along an optical beam path.

6. The method of claim 5, wherein the femtosecond laser is selected from a list of: a single femtosecond laser combined with a delay stage, and a dual femtosecond laser.

7. The method of claim 5, wherein the femtosecond laser generates the optical beam at a wavelength selected from: ~800 nm, 1550 nm.

8. The method of claim 5, wherein the plurality of optical lenses adjusts a spot size of the optical beam to cover a active area of the terahertz source and the terahertz detector.

9. The method of claim 4, wherein the terahertz scanner further comprises a plurality of terahertz lenses and or off-axis parabolic mirrors for focusing and or collimating the terahertz beam along the terahertz beam path.

10. The method of claim 9, wherein the plurality of terahertz lenses is made from a material selected from a list of: polyethylene, TPX, ceramic, Teflon, and any combination thereof.

11. The method of claim 4, wherein the characteristic signal and the reference signal are in time domain.

12. The method of claim 11, wherein the characteristic signal and the reference signal in time domain are used to find their corresponding signals in frequency-domain; and extracting the characteristic features and the corresponding reference features in both a time domain and a frequency domain.

13. The method of claim 1, wherein the chemical or structural variations are selected from a list consisting of: chemical contamination, material defects, other irregularities in a material, and any combination thereof.

14. The method of claim 13, wherein the chemical contamination comprises a toxin.

15. The method of claim 14, wherein the toxin is selected from a group consisting of: mycotoxins, aflatoxins, or a combination thereof.

16. The method of claim 13, wherein the material defects are further selected from a list consisting of: thickness variations, voids, cracks, non-uniformities, and any combination thereof.

17. The method of claim 1, wherein the sample comprises a battery electrode and the chemical or structural variations are material defects.

18. The method of claim 1, wherein the sample comprises a composite material and the chemical or structural variations are material defects.

19. The method of claim 1, wherein the at least one terahertz detector is selected from a list consisting of: a single-pixel terahertz detector, a focal plane 1D or 2D array comprising a plurality of terahertz detectors.

20. The method of claim 1, wherein the at least one terahertz detector is capable of taking three-dimensional terahertz snapshots of an area as large as ~10 $cm^2$ within less than a 100 ms.

21. The method of claim 1, wherein the at least one terahertz source and the at least one terahertz detector comprise plasmonic electrodes.

22. The method of claim 21, wherein the at least one terahertz source and the at least one terahertz detector are fabricated on a semiconductor substrate and optimized for operation at 800 nm or 1550 nm wavelengths.

23. The method of claim 21, wherein the at least one terahertz source and the at least one terahertz detector are fabricated on a GaAs, InGaAs and InAs substrate.

24. The method of claim 1, wherein the sample is placed on a sample holder selected from a list of: a moving conveyor belt, a single or multi-well plate or multiple plates mounted on a motorized translational stage, and any combination thereof.

* * * * *